United States Patent
Huang et al.

(10) Patent No.: US 9,581,595 B2
(45) Date of Patent: Feb. 28, 2017

(54) COMPOSITIONS AND METHODS FOR DETERMINING WHETHER A SUBJECT WOULD BENEFIT FROM CO-RECEPTOR INHIBITOR THERAPY

(75) Inventors: Wei Huang, Foster City, CA (US); Signe Fransen, San Francisco, CA (US); Christos Petropoulos, Half Moon Bay, CA (US); Jonathan Toma, San Francisco, CA (US); Jeannette Whitcomb, San Mateo, CA (US)

(73) Assignee: LABORATORY CORPORATION OF AMERICA HOLDINGS, Burlington, NC (US)

( * ) Notice: Subject to any disclaimer, the term of this patent is extended or adjusted under 35 U.S.C. 154(b) by 769 days.

(21) Appl. No.: 12/527,863

(22) PCT Filed: Feb. 26, 2008

(86) PCT No.: PCT/US2008/002497
§ 371 (c)(1),
(2), (4) Date: Mar. 11, 2010

(87) PCT Pub. No.: WO2008/106115
PCT Pub. Date: Sep. 4, 2008

(65) Prior Publication Data
US 2010/0167266 A1    Jul. 1, 2010

Related U.S. Application Data

(60) Provisional application No. 60/903,655, filed on Feb. 26, 2007.

(51) Int. Cl.
*G01N 33/00* (2006.01)
*G01N 33/569* (2006.01)

(52) U.S. Cl.
CPC ... *G01N 33/56988* (2013.01); *G01N 2333/16* (2013.01); *G01N 2800/52* (2013.01)

(58) Field of Classification Search
None
See application file for complete search history.

(56) References Cited

U.S. PATENT DOCUMENTS 4,683,195 A   7/1987   Mullis et al.
4,683,202 A   7/1987   Mullis
(Continued)

FOREIGN PATENT DOCUMENTS

WO   WO 97/27319      7/1997
WO   WO 2008/106115   9/2008

OTHER PUBLICATIONS

Trouplin, et al. Determination of Coreceptor Usage of Human Immunodeficiency Virus Type 1 from Patient Plasma Samples by Using a Recombinant Phenotypic Assay. J. Virol. 2001; 75(1) :251-259.*

(Continued)

*Primary Examiner* — Janet L Andres
*Assistant Examiner* — Stuart W Snyder
(74) *Attorney, Agent, or Firm* — Kilpatrick Townsend & Stockton LLP

(57) ABSTRACT

The present invention provides methods and compositions for determining whether a subject would benefit from co-receptor inhibitor therapy. In certain aspects, the methods can be used to determine whether a subject infected with a dual-mixed tropic population of HIV would benefit from CCCR5-inhibitor therapy or CXCR4-inhibitor therapy, the methods comprising determining whether the HIV population is a homogeneous or heterogeneous population of HIV, wherein the nature of the homogenous or heterogenous (Continued)

Figure 1B:
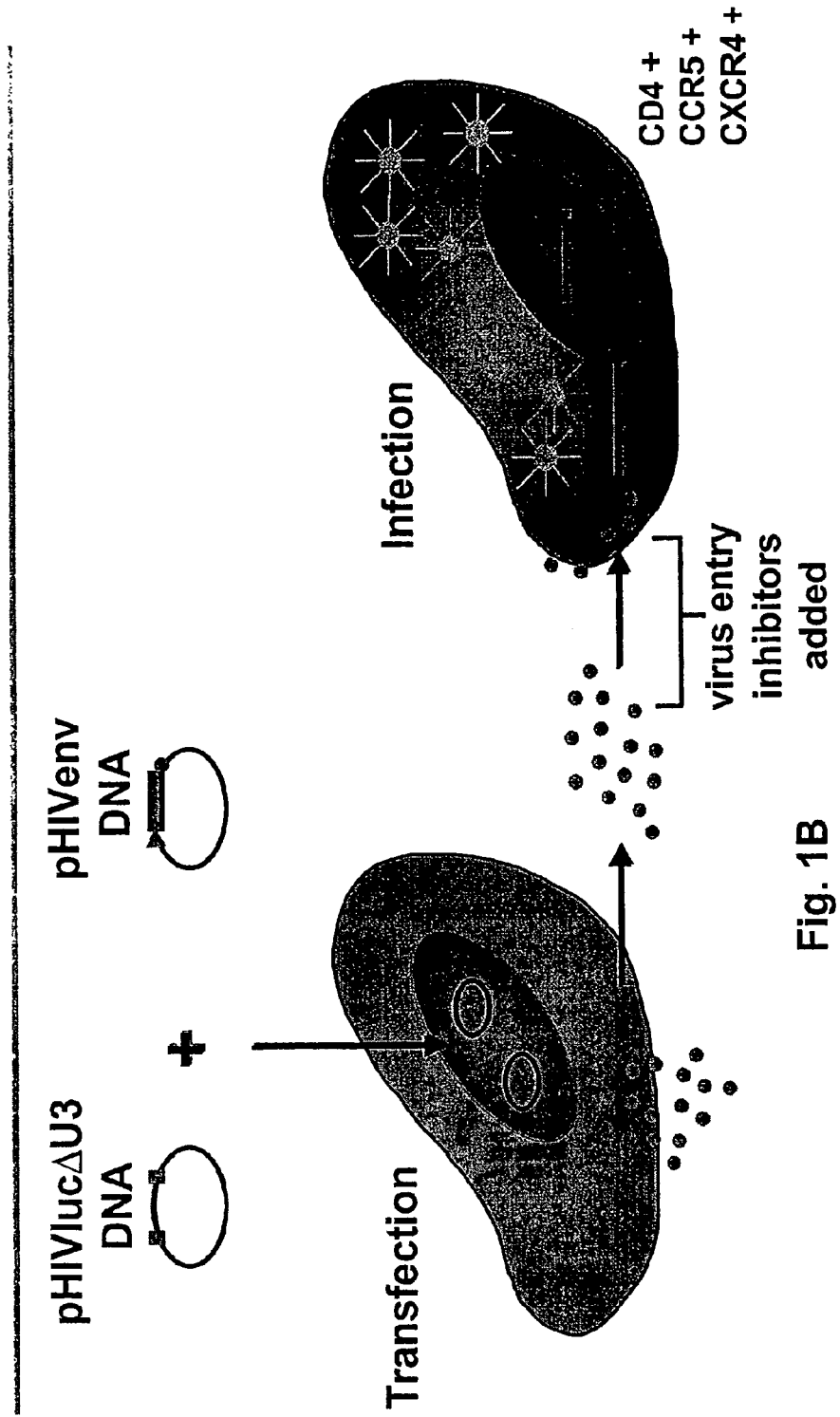

population of HIV indicates whether the patient would benefit from co-receptor inhibitor therapy.

32 Claims, 12 Drawing Sheets

(56) References Cited

U.S. PATENT DOCUMENTS

| | | |
|---|---|---|
| 4,800,159 A | 1/1989 | Mullis et al. |
| 4,965,188 A | 10/1990 | Mullis et al. |
| 5,631,734 A | 5/1997 | Stern et al. |
| 5,723,320 A | 3/1998 | Dehlinger |
| 5,744,305 A | 4/1998 | Fodor et al. |
| 5,834,758 A | 11/1998 | Trulson et al. |
| 5,837,464 A | 11/1998 | Capon et al. |
| 5,837,832 A | 11/1998 | Chee et al. |
| 5,919,523 A | 7/1999 | Sundberg et al. |
| 6,022,963 A | 2/2000 | McGall et al. |
| 6,040,138 A | 3/2000 | Lockhart et al. |
| 6,141,096 A | 10/2000 | Stern et al. |
| 6,156,501 A | 12/2000 | McGall et al. |
| 6,168,948 B1 | 1/2001 | Anderson et al. |
| 6,197,506 B1 | 3/2001 | Fodor et al. |
| 6,225,625 B1 | 5/2001 | Pirrung et al. |
| 6,261,776 B1 | 7/2001 | Pirrung et al. |
| 6,284,456 B1 | 9/2001 | Jones et al. |
| 6,287,850 B1 | 9/2001 | Besemer et al. |
| 6,291,183 B1 | 9/2001 | Pirrung et al. |
| 6,308,170 B1 | 10/2001 | Balaban |
| 6,309,823 B1 | 10/2001 | Cronin et al. |
| 6,333,155 B1 | 12/2001 | Lockhart et al. |
| 6,342,355 B1 | 1/2002 | Hacia et al. |
| 6,355,432 B1 | 3/2002 | Fodor et al. |
| 6,379,895 B1 | 4/2002 | Fodor et al. |
| 6,391,550 B1 | 5/2002 | Lockhart et al. |
| 6,410,229 B1 | 6/2002 | Lockhart et al. |
| 6,451,536 B1 | 9/2002 | Fodor et al. |
| 6,489,114 B2 | 12/2002 | Laayoun et al. |
| 6,505,125 B1 | 1/2003 | Ho |
| 6,548,257 B2 | 4/2003 | Lockhart et al. |
| 6,551,784 B2 | 4/2003 | Fodor et al. |
| 6,617,112 B2 | 9/2003 | Beals |
| 6,670,124 B1 | 12/2003 | Chow et al. |
| 6,902,921 B2 | 6/2005 | Srinivasan et al. |
| 6,956,114 B2 | 10/2005 | Srinivasan et al. |
| 7,097,970 B2 | 8/2006 | Petropoulos et al. |
| 7,169,551 B2 | 1/2007 | Petropoulos et al. |
| 7,235,356 B2 | 6/2007 | Petropoulos et al. |

OTHER PUBLICATIONS

Statistical methods for research workers. 1925. Oliver and Boyd. Edinburgh and London—Chapter 1.*

Hendrix, et al. Safety, Pharmacokinetics, and Antiviral Activity of AMD3100, a Selective CXCR4 Receptor Inhibitor, in HIV-1 Infection. J. Acquir. Immune Defic. Syndr. 2004; 37:1253-1262.*

Björndal, et al. Coreceptor Usage of Primary Human Immunodeficiency Virus Type 1 Isolates Varies According to Biological Phenotype. J. Virol. 1997; 71(10):7478.*

Muthumani, et al. Vpr-GFP Virion Particle Identifies HIV-Infected Targets and Preserves HIV-1Vpr Function in Macrophages and T-Cells. DNA Cell Biol. 2000; 19(3): 179-188.*

Gervaix, et al. A new reporter cell line to monitor HIV infection and drug susceptibility in vitro. Proc. Natl. Acad. Sci. 1997; 94: 4653-4658.*

Polianova, et al. Chemokine receptor-5 (CCR5) is a receptor for the HIV entry inhibitor peptide T (DAPTA). Antiviral Res. 2005; 67: 83-92.*

Abravaya, K. et al., "Detection of point mutations with a modified ligase chain reaction (Gap-LCR)," 1995, Nucl. Acids Res., 23:675-682.

Adachi, A. et al., "Production of Acquired Immunodeficiency Syndrome-Associated Retrovirus in Human and Nonhuman Cells Transfected with an Infectious Molecular Clone," 1986, J. Virol., 59:284-291.

Alkhatib, G. et al., "CC CKR5: A RANTES, MIP-1 α, MIP-1 β Receptor as a Fusion Cofactor for Macrophage—Tropic HIV-1," 1996, Science, 272:1955-1958.

Allaway, G.P. et al., "Synergistic Inhibition of HIV-1 Envelope-Mediated Cell Fusion by CD4-Based Molecules in Combination with Antibodies to gp120 or gp41," 1993, Aids Res. Hum. Retroviruses, 9:581-587.

Altschul, S. et al., "Basic Local Alignment Search Tool," 1990, J. Mol. Biol., 215:403-410.

Altschul, S. et al., "Gapped BLAST and PSI-BLAST: a new generation of protein database search programs," 1997, Nucleic Acids Res., 25:3389-3402.

Baba, M. et al., "A small-molecule, nonpeptide CCR5 antagonist with highly potent and selective anti-HIV-1 activity," 1999, Proc. Natl. Acad. Sci. USA, 96:5698-703.

Barnes, W.M., "PCR amplification of up to 35-kb DNA with high fidelity and high yield from λ bacteriophage templates," 1994, Proc. Natl. Acad. Sci. USA, 91:2216-2220.

Barany, F., "Genetic disease detection and DNA amplification using cloned thermostable ligase," 1991, Proc. Natl. Acad. Sci. USA, 88:189-193.

Baxter, J.D. et al., "A pilot study of the short-term effects of antiretroviral management based on plasma genotypic antiretroviral resistance testing (GART) in patients failing antiretroviral therapy," (Abstract No. LB8), Jan. 31-Feb. 4, 1999, Presented at the 6th Conf. on Retroviruses and Opportunistic Infections, Chicago, IL.

Bernard, P. and Couturier, M., "Cell Killing by the F Plasmid CcdB Protein Involves Poisoning of DNA-Topoisomerase II Complexes," 1992, J. Mol. Bio., 226:735-745.

Bernard, P. et al., "The F Plasmid CcdB Protein Induces Efficient ATP-Dependent DNA Cleavage by Gyrase," 1993, J. Mol. Biol., 23:534-541.

Bleul, C.C. et al., "The lymphocyte chemoattractant SDF-1 is a ligand for LESTR/fusin and blocks HIV-1 entry," 1996, Nature, 382:829-833.

Bridger, G.J. et al., "Synthesis and Structure—Activity Relationships of Phenylenebis(methylene)-Linked Bis-azamacrocycles That Inhibit HIV-1 and HIV-2 Replication by Antagonism of the Chemokine Receptor CXCR4," 1999, J. Med. Chem., 42:3971-3981.

Carpenter, C.J. et al., "Antiretroviral Therapy in Adults: Updated Recommendations of the International AIDS Society—USA Panel," 2000, JAMA, 283:381-391.

Centers for Disease Control & Prevention, HIV/AIDS Surveillance Report, 1999, 11 (No. 1); 42 pages.

Coffin, J.M., "HIV Population Dynamics in Vivo: Implications for Genetic Variation, Pathogenesis, and Therapy," 1995, Science, 267:483-489.

Cotton, R. et al., "Reactivity of cytosine and thymine in single-base-pair mismatches with hydroxylamine and osmium tetroxide and its application to the study of mutations," 1988, Proc. Natl. Acad. Sci. USA, 85:4397-4401.

Current Protocols in Molecular Biology, Ausubel, F.M. et al., eds., John Wiley & Sons, NY, 2010 Table of Contents and list of yearly supplements.

Department of Health and Human Services (DHHS), Henry Kaiser Family Foundation, "Guidelines for the Use of Antiretroviral Agents in HIV-Infected Adults and Adolescents," Jan. 28, 2000.

Eisenberg, D. et al. "Analysis of Membrane and Surface Protein Sequences with the Hydrophobic Moment Plot," 1984, J. Mol. Biol., 179:125-142.

Faham, M. and Cox, D., "A Novel In Vivo Method to Detect DNA Sequence Variation," 1995, Genome Res., 5:474-482.

Fisher, S.G. and Lerman, L.S., "DNA fragments differing by single nucleotide base-pair substitutions are separated in denaturing gradient gels: Correspondence with melting theory," 1983, Proc. Natl. Acad. Sci. USA, 80:1579-1583.

GenBank Accession No. AF324493, "HIV-1 vector pNL4-3," complete sequence, 1986, submitted to GenBank Feb. 15, 2001.

(56) References Cited

OTHER PUBLICATIONS

Gerdes, K. et al., "The hok Killer Gene Family in Gram-Negative Bacteria," 1990, The New Biologist, 2:946-956.
Hendrix et al., "Safety, Pharmacokinetics, and Antiviral Activity of AMD3100, a Selective CXCR4 Receptor Inhibitor, in HIV-1 Infection," 2004, J. Acquir. Immune Defic. Syndr., 37:1253-1262.
Hertogs, K. et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs," 1998, Antimicrob. Agents Chemother., 42:269-276.
Hwang, J-J. et al., "A Conditional Self-Inactivating Retrovirus Vector That Uses a Tetracycline-Responsive Expression System," 1997, J. Virol., 71:7128-7131.
Japour, A.J. et al., "Standardized Peripheral Blood Mononuclear Cell Culture Assay for Determination of Drug Susceptibilities of Clinical Human Immunodeficiency Virus Type 1 Isolates," 1993, Antimicrob. Agents Chemother., 37:1095-1101.
Judice, J.K. et al., "Inhibition of HIV type 1 infectivity by constrained α-helical peptides: Implications for the viral fusion mechanism," 1997, Proc. Natl. Acad. Sci. USA, 94:13426-13430.
Kan, Y. and Dozy, A. "Antenatal Diagnosis of Sickle-Cell Anemia by D.N.A. Analysis of Amniotic-Fluid Cells," 1978, Lancet, 2:910-912.
Kilby, J.M. et al., "Potent suppression of HIV-1 replication in humans by T-20, a peptide inhibitor of gp41-mediated virus entry," 1998, Nat. Med., 4:1302-1307.
Landegren, U. et al., "A Ligase-Mediated Gene Detection Technique," 1988, Science, 241:1077-1080.
Margulies, M. et al., "Genome sequencing in microfabricated high-density picolitre reactors," 2005, Nature, 437:376-380.
Mascola, J.R. et al., "Protection of macaques against vaginal transmission of a pathogenic HIV-1/SIV chimeric virus by passive infusion of neutralizing antibodies," 2000, Nature Med., 6:207-210.
Maxam, A. et al., "Sequencing End-Labeled DNA with Base-Specific Chemical Cleavages," 1980, Methods in Enzymology, 65:499-560.
Messing, J. et al., "A system for shotgun DNA sequencing," 1981, Nuc. Acids Res., 9:309-321.
Miyoshi, H. et al., "Development of a Self-Inactivating Lentivirus Vector," 1998, J. Virol., 72:8150-8157.
Myers, R. et al., "Detection of Single Base Substitutions by Ribonuclease Cleavage at Mismatches in RNA:DNA Duplexes," 1985, Science, 230:1242-1246.
Naviaux, R.K. et al., "The pCL Vector System: Rapid Production of Helper-Free, High-Titer, Recombinant Retroviruses," 1996, J. Virol., 70:5701-5705.
Nikiforov, T. et al., "Genetic Bit Analysis: a solid phase method for typing single nucleotide polymorphisms," 1994, Nucl. Acids. Res., 22:4167-4175.
Orita, M. et al., "Rapid and Sensitive Detection of Point Mutations and DNA Polymorphisms Using the Polymerase Chain Reaction," 1989, Genomics, 5:874-879.
Orita, M. et al., "Detection of polymorphisms of human DNA by gel electrophoresis as single-strand conformation polymorphisms," 1989, Proc. Natl. Acad. Sci. USA, 86:2766-2770.
Orum, H. et al., "Single base pair mutation analysis by PNA directed PCR clamping," 1993, Nucl. Acids Res., 21:5332-5336.
PCR Strategies, 1995, Innis, M.A. et al., eds., Academic Press, Inc., San Diego, CA.
Petropoulos, C. et al., "A Novel Phenotypic Drug Susceptibility Assay for Human Immunodeficiency Virus Type 1," 2000, Antimicrob. Agents & Chemother., 44:920-928.
Piketty, C. et al., "Efficacy of a five-drug combination including ritonavir, saquinavir and efavirenz in patients who failed on a conventional triple-drug regimen: phenotypic resistance to protease inhibitors predicts outcome of therapy," 1999, AIDS, 13:F71-F77.
Porter, C.C. et al, "Cationic Liposomes Enhance the Rate of Transduction by a Recombinant Retroviral Vector In Vitro and In Vivo," 1998, J. Virol., 72:4832-4840.

Reimann, K.A. et al., "In Vivo Administration of CD4-Specific Monoclonal Antibody: Effect on Provirus Load in Rhesus Monkeys Chronically Infected with the Simian Immunodeficiency Virus of Macaques," 1995, Aids Res. Hum. Retroviruses, 11:517-525.
Richman, D., "Nailing down another HIV target," 1998, Nature Med., 4:1232-1233.
Rimsky, L.T. et al., "Determinants of Human Immunodeficiency Virus Type 1 Resistance to gp41-Derived Inhibitory Peptides," 1998, J. Virol., 72:986-993.
Rodriquez-Rosado, R. et al., "Introduction of HIV drug-resistance testing in clinical practice," 1999, AIDS, 13:1007-1014.
Russell, W. et al., "Specific-locus test shows ethylnitrosourea to be the most potent mutagen in the mouse," 1979, Proc. Nat. Acad. Sci. USA, 76:5818-5819.
Russell, W., "Factors Affecting Mutagenicity of Ethylnitrosourea in the Mouse Specific-Locus Test and Their Bearing on Risk Estimation," Environmental Mutagens and Carcinogens: Proceedings of the Third International Conference on Environmental Mutagens, 1982.
Sambrook, J. and Russell, D.W., Molecular Cloning: A Laboratory Manual, 2001, 3rd ed., Cold Spring Harbor Laboratory, New York, NY.
Sanger, F. et al., "DNA sequencing with chain-terminating inhibitors," 1977, Proc. Natl. Acad. Sci. USA, 74:5463-5467.
Sarkar, G. and Sommer, S.S., "The 'Megaprimer' Method of Site-Directed Mutagenesis," 1990, BioTechniques, 8:404-407.
Schinazi, R.F. et al., "Mutations in retroviral genes associated with drug resistance: 1999-2000 update," 1999, Intl. Antiviral News, 7:46-69.
Shi, C. and Mellors, J., "A Recombinant Retroviral System for Rapid In Vivo Analysis of Human Immunodeficiency Virus Type 1 Susceptibility to Reverse Transcriptase Inhibitors," 1997, Antimicrob. Agents Chemother., 41:2781-2785.
Southern, E.M., "Detection of Specific Sequences Among DNA Fragments Separated by Gel Electrophoresis," 1975, J. Mol. Biol., 98:503-517.
Stephenson, J., "New Class of Anti-HIV Drugs," 1999, JAMA, 282:1994.
Syvanen, A-C. et al., "A Primer-Guided Nucleotide Incorporation Assay in the Genotyping of Apolipoprotein E", 1990, Genomics, 8:684-692.
Thiede, C. et al., "Simple and sensitive detection of mutations in the ras proto-oncogenes using PNA-mediated PCR clamping," 1996, Nucl. Acids Res., 24:983-984.
Wagner, R. et al., "Mutation detection using immobilized mismatch binding protein (MutS)," 1995, Nucl. Acids Res., 23:3944-3948.
WHO, Unaids/ World Health Organization, "Report: Aids Epidemic Update," Dec. 1999.
Wild, C. et al., "A synthetic peptide inhibitor of human immunodeficiency virus replication: Correlation between solution structure and viral inhibition," 1992, Proc. Natl. Acad. Sci. USA, 89:10537-10541.
Youil, R. et al., "Screening for mutations by enzyme mismatch cleavage with T4 endonuclease VII," 1995, Proc. Natl. Acad. Sci. USA, 92:87-91.
Zennou, V. et al., "Loss of Viral Fitness Associated with Multiple Gag and Gag-Pol Processing Defects in Human Immunodeficiency Virus Type 1 Variants Selected for Resistance to Protease Inhibitors In Vivo," 1998, J. Virol., 72:3300-3306.
Ziermann, R. et al., "A Mutation in Human Immunodeficiency Virus Type 1 Protease, N88S, That Causes In Vitro Hypersensitivity to Amprenavir," 2000, J. Virol., 74:4414-4419.
International Search Report mailed Oct. 7, 2008 corresponding to Application No. PCT/US08/02497.
Written Opinion of the International Searching Authority mailed Oct. 7, 2008 corresponding to Application No. PCT/US08/02497.
Colonno, R. et al., "Identification of I50L as the Signature Atazanavir (ATV)-Resistance Mutation in Treatment-Naïve HIV-1-Infected Patients Receiving ATV-Containing Regimens," 2004, J. Infectious Diseases, 189:1802-1810.

(56) References Cited

OTHER PUBLICATIONS

Gupta, S. et al., "Combinations of Mutations in the Connection Domain of Human Immunodeficiency Virus Type 1 Reverse Transcriptase: Assessing the Impact on Nucleoside and Non-nucleoside Reverse Transcriptase Inhibitor Resistance," 2010, Antimicrob. Agents and Chemother., 54:1973-1980.

Hirsh, M. et al., "Antiretroviral Drug Resistance Testing in Adult HIV-1 Infection: 2008 Recommendations of an International AIDS Society—USA Panel," 2008, Clinical Infectious Diseases, 47:266-285.

Kroodsma, K. et al., "Detection of Drug Resistance Mutations in the Human Immunodeficiency Virus per 1 (HIV-1) pol Gene: Differences in Semen and Blood HIV-1 RNA and Proviral DNA," 1994, J. Infectious Diseases, 170:1292-1295.

Mellors, J. et al., "Mutations in HIV-1 Reverse Transcriptase and Protease Associated with Drug Resistance," 1995, Mutations in RT and Protease, III:93-105.

\* cited by examiner

PhenoSense HIV Entry Assay
Envelope Expression Vector: pHIVenv
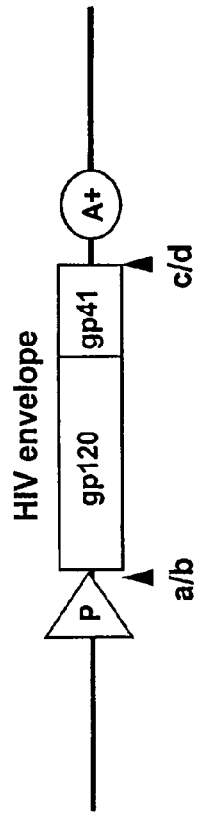
HIV-1 Expression Vector: pHIVlucΔU3
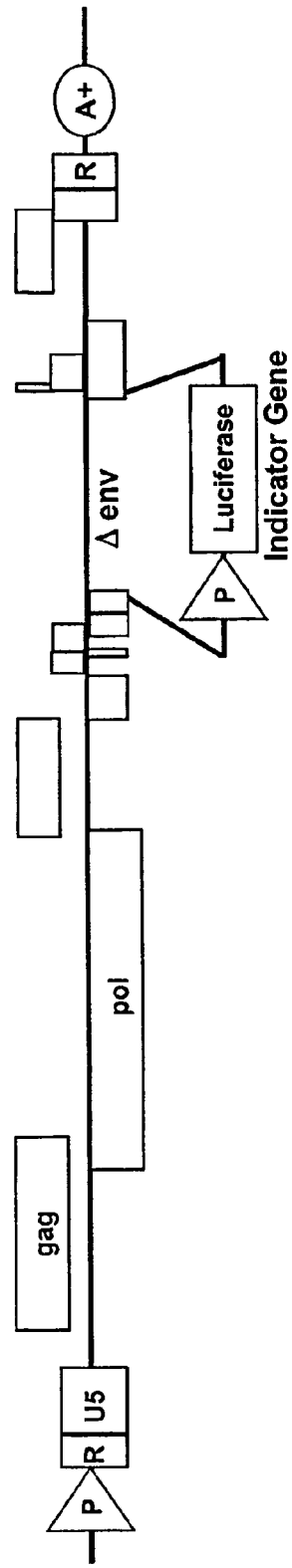
Fig. 1A

Figure 8

| GROUP | Subject | Dose | Baseline RLU R5 | Baseline RLU X4 | Day 11 RLU R5 | Day 11 RLU X4 |
|---|---|---|---|---|---|---|
| SUPPRESSOR | 74 | 80 | 52546 | 308 | 87159 | 56 |
| SUPPRESSOR | 31 | 20 | 114206 | 575 | 316970 | 107 |
| SUPPRESSOR | 9 | 5 | 39,361 | 998 | 50,543 | 112 |
| SUPPRESSOR | 32 | 40 | 46180 | 1904 | 140449 | 107 |
| SUPPRESSOR | 28 | 20 | 409212 | 2046 | 384574 | 81 |
| SUPPRESSOR | 35 | 40 | 34494 | 2443 | 153409 | 56 |
| SUPPRESSOR | 73 | 80 | 143194 | 3021 | 134000 | 97 |
| SUPPRESSOR | 11 | 5 | 224031 | 13710 | 256901 | 199 |
| SUPPRESSOR | 10 | 5 | 813,948 | 32,597 | 932,650 | 77 |
| SUPPRESSOR | 33 | 40 | 241910 | 48606 | 170994 | 505 |
| NON-SUPPRESSOR | 70 | 40 | 124598 | 216896 | 157147 | 256772 |
| NON-SUPPRESSOR | 2 | 2.5 | 272689 | 342258 | 346774 | 496095 |
| NON-SUPPRESSOR | 21 | 10 | 35731 | 389548 | 223413 | 209882 |
| NON-SUPPRESSOR | 71 | 40 | 720638 | 1647981 | 851150 | 1130617 |

Groups defined by X4 response at day 11

Figure 9

| GROUP | Subject | Dose | Day 11 Tropism | Baseline Composition % R5 | X4 | DUAL | Day 11 Composition % R5 | X4 | DUAL |
|---|---|---|---|---|---|---|---|---|---|
| SUPPRESSOR | 74 | 80 | R5 | 95 | 0 | 5 | 100 | 0 | 0 |
| SUPPRESSOR | 31 | 20 | R5 | 92 | 4 | 4 | 100 | 0 | 0 |
| SUPPRESSOR | 9 | 5 | R5 | 93 | 0 | 7 | 98 | 0 | 2 |
| SUPPRESSOR | 32 | 40 | R5 | 80 | 0 | 20 | 94 | 0 | 6 |
| SUPPRESSOR | 28 | 20 | R5 | 72 | 14 | 14 | 100 | 0 | 0 |
| SUPPRESSOR | 35 | 40 | R5 | 61 | 39 | 0 | 100 | 0 | 0 |
| SUPPRESSOR | 73 | 80 | R5 | 82 | 3 | 15 | 100 | 0 | 0 |
| SUPPRESSOR | 11 | 5 | DM | 52 | 0 | 48 | 97 | 0 | 3 |
| SUPPRESSOR | 10 | 5 | R5 | 65 | 15 | 20 | 98 | 0 | 2 |
| SUPPRESSOR | 33 | 40 | DM | 57.5 | 7.5 | 35 | 85 | 0 | 15 |
| NON-SUPPRESSOR | 70 | 40 | DM | 0 | 0 | 100 | 0 | 0 | 100 |
| NON-SUPPRESSOR | 2 | 2.5 | DM | 8 | 0 | 92 | 10 | 0 | 90 |
| NON-SUPPRESSOR | 21 | 10 | DM | 0 | 58 | 42 | 0 | 0 | 100 |
| NON-SUPPRESSOR | 71 | 40 | DM | 0 | 0 | 100 | 0 | 0 | 100 |

Groups defined by X4 response at day 11

COMPOSITIONS AND METHODS FOR DETERMINING WHETHER A SUBJECT WOULD BENEFIT FROM CO-RECEPTOR INHIBITOR THERAPY

CROSS REFERENCE TO RELATED APPLICATIONS

This application is a U.S. National Stage application of International Application No. PCT/US2008/002497, filed 26 Feb. 2008, which claims the benefit of U.S. Patent Application No. 60/903,655 filed 26 Feb. 2007, the contents of which are incorporated herein by reference in their entirety.

Throughout this application, various publications are referenced by author and date within the text. Full citations for these publications may be found listed alphabetically at the end of the specification immediately preceding the claims. All patents, patent applications and publications cited herein are hereby incorporated by reference in their entirety.

1. BACKGROUND

Enveloped animal viruses attach to and enter the host cell via the interaction of viral proteins in the virion membrane (envelope proteins) and cell surface proteins (virus receptors). Receptor recognition and binding are mediated by the surface envelope protein. Virus entry is an attractive target for anti-viral treatment; numerous entry inhibitor drugs that are designed to block HIV receptor (CD4) attachment, co-receptor (CCR5, CXCR4) engagement, or host cell-virus membrane fusion have been or are currently being evaluated in preclinical or clinical studies (Richman, 1998; PhRMA, 1999; Stephenson, 1999). For example, the co-receptor antagonist vicriviroc (SCH-D, Schering Plough), which blocks the interaction between the viral membrane surface protein (gp120) and CCR5, is currently being evaluated in clinical studies for its effectiveness as an anti-viral treatment (Shurman, 2004). Other entry inhibitors currently or previously under investigation include UK-427857 (maraviroc, Pfizer), TNX-355 (Tanox Inc.), AMD-11070 (AnorMED), Pro 140 and Pro 584 (Progenies), FP-21399 (EMD Lexigen), BMS-488043 (Bristol-Myers Squibb), INCB9471 (Incyte), KRH-3955 and KRH-314 (Kureha), HGSImAb004 (Human Genome Sciences), TRI-999, (Trimeris) and GSK-873,140 (aplaviroc, GlaxoSmithKline). One entry inhibitor, FUZEON® (enfuvirtide; Roche/Trimeris), has been approved for treatment of HIV infection by the United States Food and Drug Administration.

As these drugs continue to be developed and enter the clinic, assays are needed that can rapidly and easily identify patient populations that may clinically benefit from administration of these drugs. These and other unmet needs are provided by the present invention.

2. SUMMARY

In a first aspect, the invention provides a method for determining whether a subject with a dual-mixed tropic population of human immunodeficiency viruses (HIV) would benefit from CXCR4-inhibitor or CCR5-inhibitor therapy, comprising: a) determining whether the population is a homogeneous or heterogeneous population; wherein if the population is a homogeneous population, step b of the method is performed, and wherein if the population is a heterogeneous population, step c of the method is performed; b) determining whether the homogeneous population is Dual_R tropic or Dual_X tropic or neither (Dual tropic), wherein if the homogeneous population is composed of Dual_R tropic HIV, the subject would benefit from CCR5-inhibitor therapy, wherein if the homogeneous population is composed of Dual_X HIV, the subject would benefit from CXCR4-inhibitor therapy, and wherein if the homogeneous population is neither Dual_R tropic nor Dual_X, the subject would not benefit from either CCR5-inhibitor or CXCR4-inhibitor therapy; and c) determining the relative proportions of CCR5-tropic, CXCR4-tropic, Dual_R-tropic, Dual_X-tropic, or Dual tropic HIV of the heterogeneous population, wherein if the heterogeneous population contains i) CCR5-tropic and/or Dual_R-tropic, and ii) CXCR4-tropic and/or Dual_X-tropic HIV and comprises substantially more CCR5-tropic and/or Dual_R-tropic HIV than CXCR4-tropic and/or Dual_X-tropic HIV, the subject would benefit from CCR5-inhibitor therapy;

if the heterogeneous population contains i) CCR5-tropic and/or Dual_R tropic, and ii) CXCR4-tropic and/or Dual_X tropic HIV and comprises comparable amounts of CCR5-tropic and/or Dual_R tropic and CXCR4-tropic and/or Dual_X tropic HIV, the subject would not benefit from either CCR5-inhibitor or CXCR4-inhibitor therapy;

if the heterogeneous population contains 1) CCR5-tropic and/or Dual_R tropic, and ii) CXCR4-tropic and/or Dual_X tropic HIV and comprises substantially more CXCR4-tropic and/or Dual_X tropic HIV than CCR5-tropic and/or Dual_R tropic HIV, the subject would benefit from CXCR4-inhibitor therapy;

if the heterogeneous population contains i) CCR5-tropic and/or Dual_R tropic, and ii) dual-tropic HIV and comprises substantially more CCR5-tropic and/or Dual_R tropic HIV than dual-tropic HIV, the subject would benefit from CCR5-inhibitor therapy;

if the heterogeneous population contains i) CCR5-tropic and/or Dual_R tropic, and ii) dual-tropic HIV and comprises relatively comparable amounts of CCR5-tropic and/or Dual_R tropic HIV and dual-tropic HIV or comprises substantially more dual-tropic HIV than CCR5-tropic and/or Dual_R tropic HIV, the subject would not benefit from CCR5-inhibitor or CXCR4-inhibitor therapy;

if the heterogeneous population contains i) CXCR4-tropic and/or Dual_X tropic, and ii) dual-tropic HIV and comprises substantially more CXCR4-tropic and/or Dual_X tropic HIV than dual-tropic HIV, the subject would benefit from CXCR4-inhibitor therapy;

if the heterogeneous population contains i) CXCR4-tropic and/or Dual_X tropic, and ii) dual-tropic HIV and comprises relatively comparable amounts of CXCR4-tropic and/or Dual_X tropic HIV and dual-tropic HIV or comprises substantially more dual-tropic HIV than CXCR4-tropic and/or Dual_X tropic HIV, the subject would not benefit from either CXCR4-inhibitor or CCR5-inhibitor therapy;

if the heterogeneous population contains i) CCR5-tropic and/or Dual_R tropic, ii) CXCR4-tropic and/or Dual_X tropic, and iii) dual-tropic HIV and comprises substantially more CCR5-tropic and/or Dual_R tropic HIV than CXCR4-tropic and/or Dual_X tropic and dual-tropic HIV, the subject would benefit from CCR5-inhibitor therapy;

if the heterogeneous population contains i) CCR5-tropic and/or Dual_R tropic, ii) CXCR4-tropic and/or Dual_X tropic, and iii) dual-tropic HIV and comprises relatively comparable amounts of CCR5-tropic and/or Dual_R tropic HIV and CXCR4-tropic and/or Dual_X tropic and dual-tropic HIV, the subject would not benefit from either CCR5-inhibitor or CXCR4-inhibitor therapy; and if the heterogeneous population contains i) CCR5-tropic and/or Dual_R tropic, ii) CXCR4-tropic and/or Dual_X tropic, and iii) dual-tropic HIV and comprises substantially more CXCR4-tropic and/or Dual_X tropic HIV than CCR5-tropic and/or Dual_R tropic and dual-tropic HIV, the subject would benefit from CXCR4-inhibitor therapy.

In certain embodiments, the population is a homogeneous population of dual tropic viruses. In certain embodiments, the homogeneous population is Dual_R-tropic. In certain embodiments, the homogeneous population is Dual_X-tropic. In certain embodiments, the homogeneous population is neither Dual_R-tropic nor Dual_X-tropic.

In certain embodiments, the population is a heterogeneous population of mixed virus tropisms. In certain embodiments, the heterogeneous population contains CCR5-tropic and/or Dual_R tropic and CXCR4-tropic and/or Dual_X tropic HIV. In certain embodiments, the population comprises substantially more CCR5-tropic and/or Dual_R tropic HIV than CXCR4-tropic and/or Dual_X tropic HIV. In certain embodiments, the population comprises comparable amounts of CCR5-tropic and/or Dual_R tropic and CXCR4-tropic and/or Dual_X tropic HIV. In certain embodiments, the population comprises substantially more CXCR4-tropic and/or Dual_X tropic HIV than CCR5-tropic and/or Dual_R tropic HIV.

In certain embodiments, the heterogeneous population contains CCR5-tropic and/or Dual_R tropic and dual-tropic HIV. In certain embodiments, the population comprises substantially more CCR5-tropic and/or Dual_R tropic HIV than dual-tropic HIV. In certain embodiments, the population comprises relatively comparable amounts of CCR5-tropic and/or Dual_R tropic HIV and dual-tropic HIV. In certain embodiments, the population comprises substantially more dual-tropic HIV than CCR5-tropic and/or Dual_R tropic HIV.

In certain embodiments, the heterogeneous population contains CXCR4-tropic and/or Dual_X tropic and dual-tropic HIV. In certain embodiments, the population comprises substantially more CXCR4-tropic and/or Dual_X tropic HIV than dual-tropic HIV. In certain embodiments, the population comprises relatively comparable amounts of CXCR4-tropic and/or Dual_X tropic HIV and dual-tropic HIV. In certain embodiments, the population comprises substantially more dual-tropic HIV than CXCR4-tropic and/or Dual_X tropic HIV.

In certain embodiments, the heterogeneous population contains CCR5-tropic and/or Dual_R tropic, CXCR4-tropic and/or Dual_X tropic, and dual-tropic HIV. In certain embodiments, the population comprises substantially more CCR5-tropic and/or Dual_R tropic HIV than CXCR4-tropic and/or Dual_X tropic and dual-tropic HIV. In certain embodiments, the population comprises relatively comparable amounts of CCR5-tropic and/or Dual_R tropic HIV and CXCR4-tropic and/or Dual_X tropic and dual-tropic HIV. In certain embodiments, the population comprises substantially more CXCR4-tropic and/or Dual_X tropic HIV than CCR5-tropic and/or Dual_R tropic and dual-tropic HIV.

In certain embodiments, the step of determining whether the HIV population is a homogeneous or heterogeneous population is performed by determining a tropism phenotype for a statistically significant number of individual viruses infecting the subject. In certain embodiments, a tropism phenotype is determined for at least about 100 HIV (molecular or biological clones representing a single virus). In certain embodiments, a tropism phenotype is determined for at least about 112 HIV. In certain embodiments, a tropism phenotype is determined for at least about 125 HIV. In certain embodiments, a tropism phenotype is determined for at least about 137 HIV. In certain embodiments, a tropism phenotype is determined for at least about 150 HIV. In certain embodiments, a tropism phenotype is determined for at least about 162 HIV. In certain embodiments, a tropism phenotype is determined for at least about 175 HIV. In certain embodiments, a tropism phenotype is determined for at least about 187 HIV. In certain embodiments, a tropism phenotype is determined for at least about 192 HIV. In certain embodiments, a tropism phenotype is determined for at least about 200 HIV.

In certain embodiments, the step of determining whether the HIV population is a homogeneous or heterogeneous population is performed by evaluating the relative level of infectivity on target cells expressing CD4 and CXCR4 vs CD4 and CCR5. In certain embodiments, the step of determining whether the HIV population is a homogeneous or heterogeneous population is performed by evaluating the inhibition of viral infectivity by specific co-receptor inhibitors on cells expressing CD4 and CXCR4 vs target cells expressing CD4 and CCR5 vs target cells expressing CD4 and CXCR4 and CCR5. In certain embodiments, the step of determining whether the HIV population is a homogeneous or heterogeneous population is performed by evaluating the env genotypes of a portion of the viruses comprising the population. In some non-limiting embodiments, the method of evaluating the env genotypes is performed according to the method described in Margulies et al., 2005, *Nature* 437:376-380. In other embodiments, the method of evaluating the env genotypes can be performed by sequencing individual viral clones' env genes, or a portion thereof.

In another aspect, the invention provides a method for determining whether a subject infected with a dual-mixed tropic population of HIV would benefit from CXCR4-inhibitor therapy, comprising determining whether the HIV population is a homogeneous or heterogeneous population of HIV, wherein if the subject is infected with a homogeneous population of HIV and the homogeneous population is Dual_X tropic, the subject would benefit from CXCR4-inhibitor therapy; or if the subject is infected with a heterogeneous population of HIV and the heterogeneous population of HIV comprises substantially more CXCR4-tropic or Dual_X tropic HIV than total CCR5-tropic, Dual_R tropic, and dual-tropic HIV, the subject would benefit from CXCR4-inhibitor therapy, thereby determining whether the subject would benefit from CXCR4-inhibitor therapy.

In certain embodiments, the HIV population is homogeneous. In certain embodiments, wherein the HIV population is heterogeneous. In certain embodiments, the step of determining whether the HIV population is a homogeneous or heterogeneous population is performed by determining a tropism phenotype for a statistically significant number of individual viruses infecting the subject.

In still another aspect, the invention provides a method for determining whether a subject infected with a dual-mixed tropic population of HIV would benefit from CCR5-inhibitor therapy, comprising determining whether the HIV population is a homogeneous or heterogeneous population of HIV, wherein if the subject is infected with a homogeneous population of HIV and the homogeneous population is Dual_R tropic, the subject would benefit from CCR5-inhibitor therapy; or if the subject is infected with a heterogeneous population of HIV and the heterogeneous population of HIV comprises substantially more CCR5-tropic or Dual_R tropic HIV than total CXCR4-tropic, Dual_X tropic, and dual-tropic HIV, the subject would benefit from CCR5-inhibitor therapy, thereby determining whether the subject would benefit from CCR5-inhibitor therapy.

In certain embodiments, the HIV population is homogeneous. In certain embodiments, the HIV population is heterogeneous. In certain embodiments, the step of determining whether the HIV population is a homogeneous or heterogeneous population is performed by determining a tropism phenotype for a statistically significant number of individual viruses infecting the subject.

In another aspect, the invention provides a method for determining whether a subject infected with a dual-mixed tropic population of HIV would benefit from CCR5-inhibitor therapy and/or CXCR4-inhibitor therapy, comprising determining the primary mechanism of co-receptor usage of the dual-mixed population of HIV, and determining whether the subject would benefit from CCR5-inhibitor therapy and/or CXCR4-inhibitor therapy.

3. BRIEF DESCRIPTION OF THE FIGURES

FIG. 1A: Structure of envelope expression and viral expression vectors.

The HIV envelope expression vector (pHIVenv) is modified to accept envelope sequences that have been amplified from subject plasma samples. The designations a/b and c/d, refer to restriction endonuclease sites positioned at the 5' and 3' end of the HIV-1 envelope polyprotein (gp160). The HIV expression vector (pHIVlucΔU3) encodes all HIV proteins except the envelope polyprotein. A portion of the envelope gene has been deleted to accommodate an indicator gene cassette, in this case, firefly luciferase, that is used to monitor the ability of the virus to replicate in the presence or absence of anti-viral drugs. The 3' U3 region has been partially deleted to prevent transcription from the 5' LTR in infected cells. Virus produced in this system is limited to a single round of replication.

FIG. 1B: Cell Based Entry Assay

In this embodiment, drug susceptibility, co-receptor tropism and virus neutralization testing are performed by co-transfecting a host cell with pHIVenv and pHIVlucΔU3. The host cell produces HIV particles that are pseudo-typed with HIV envelope sequences derived from the test virus or subject sample. Virus particles are collected (~48 h) after transfection and are used to infect target cells that express HIV receptors (e.g. CD4) and co-receptors (e.g. CXCR4, CCR5). After infection (~72 h) the target cells are lysed and luciferase activity is measured. HIV must complete one round of replication to successfully infect the target host cell and produce luciferase activity. If the virus is unable to enter the target cell, luciferase activity is diminished. This system can be used to evaluate susceptibility to entry inhibitors, receptor and co-receptor tropism, and virus neutralization.

Figure 2:
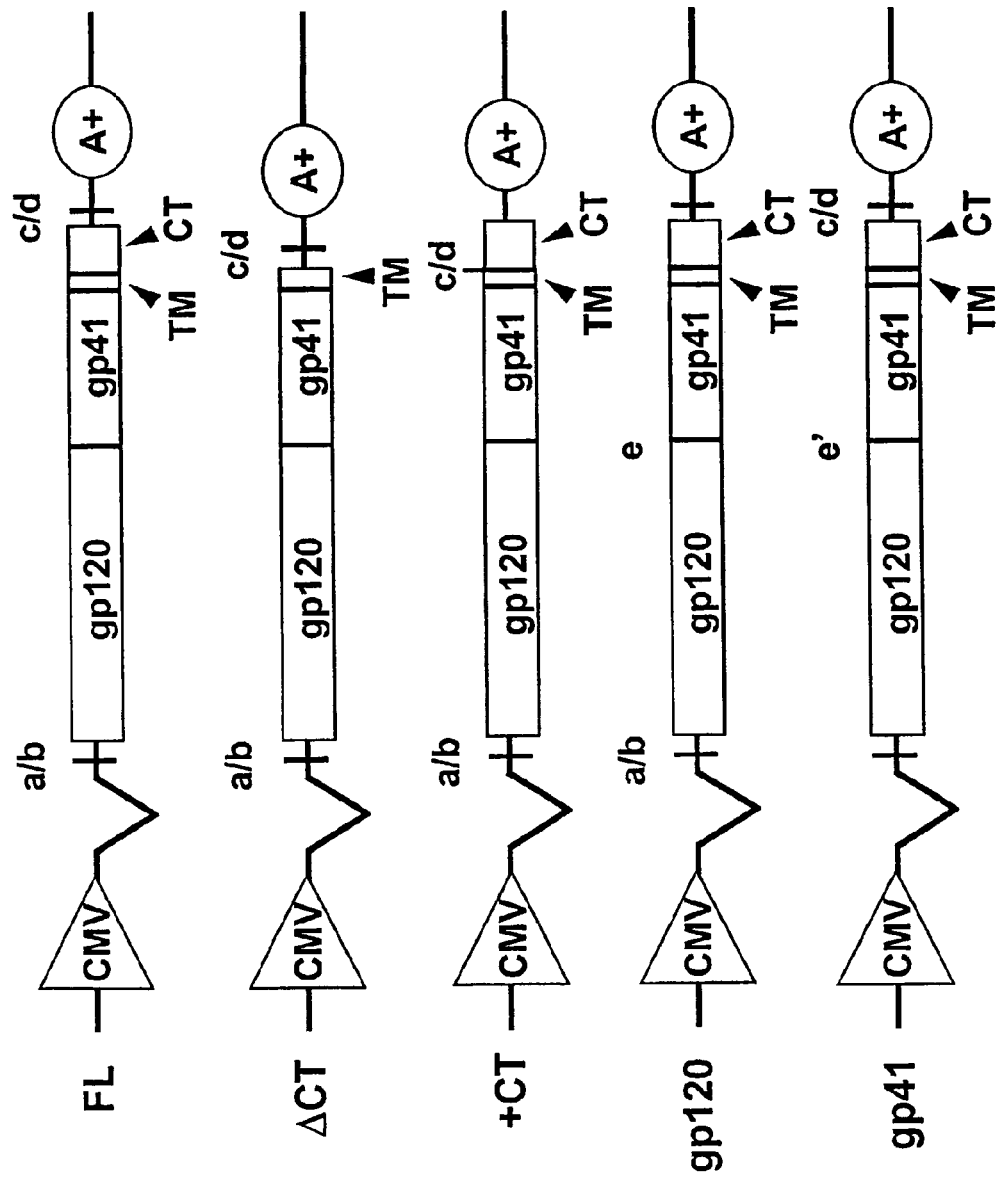

FIG. 2: HIV envelope expression vectors.

HIV envelope sequences are amplified from subject samples and inserted into expression vectors using restriction endonuclease sites (5' a/b and 3' c/d). Envelope transcription is driven by the immediate early gene promoter of human cytomegalovirus (CMV). Envelope RNA is polyadenylated using an simian virus 40 (SV4O) polyadenylation signal sequence (A+). An intron located between the CMV promoter and the HIV envelope sequences is designed to increase envelope mRNA levels in transfected cells. FL-express full-length envelope proteins (gp120, gp41); ΔCT-express envelope proteins (gp120, gp21) lacking the C-terminal cytoplasmic tail domain of gp41; +CT-express envelope proteins (gp120, gp41) containing a constant pre-defined gp41 cytoplasmic tail domain; gp120-express gp120 proteins derived from the subject together with a constant pre-defined gp41; and gp41-express a constant pre-defined gp120 together with gp41 proteins derived from the subject.

Figure 3A:
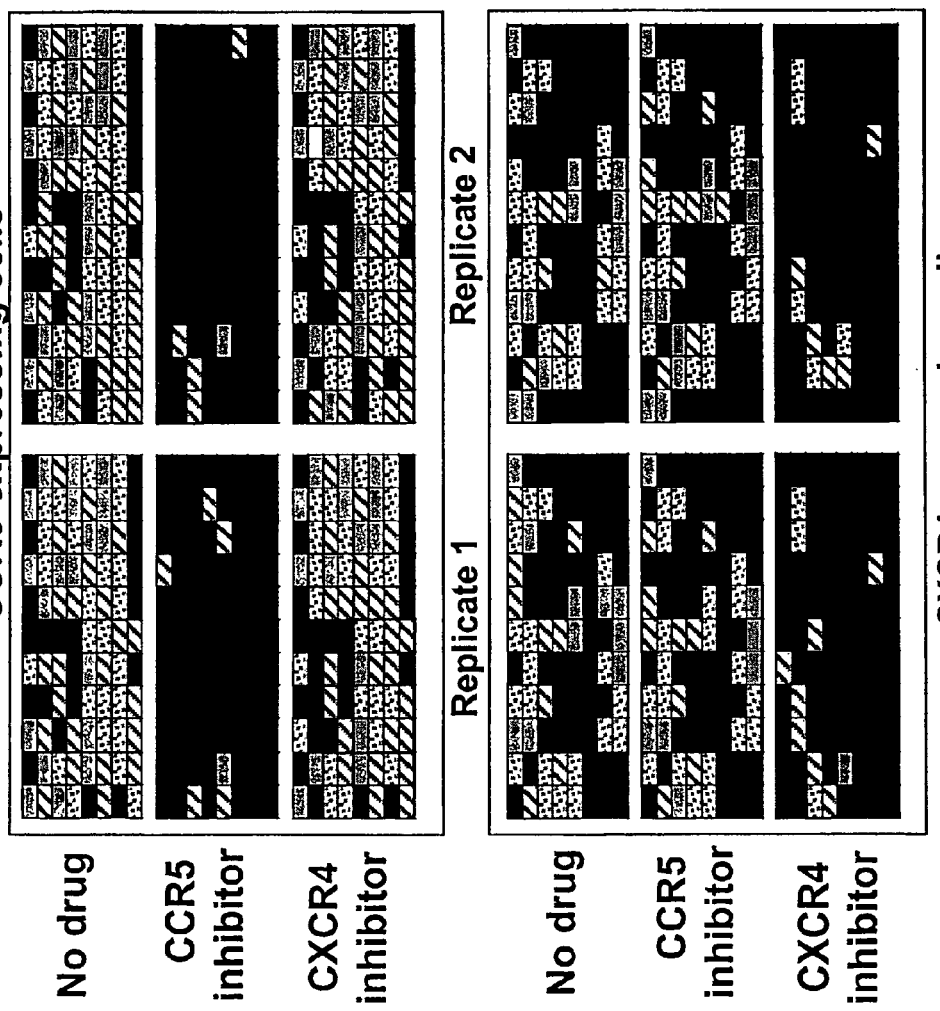

FIG. 3A: Co-receptor Tropism Screening Assay.

In this figure, the assay is performed using two cell lines. One cell line expresses CD4 and CCR5 (top six panels). The other cell line expresses CD4 and CXCR4 (bottom six panels). The assay is performed by infecting cells with a large number of recombinant virus stocks derived from cells transfected with pHIVenv and pHIVlucΔU3 vectors. The example shown represents the analysis of 96 viruses formatted in a 96 well plate infections are performed in the absence of drug (no drug), or in the presence of a drug that preferentially inhibits either R5 tropic (CCR inhibitor) or X4 tropic (CXCR4 inhibitor) viruses. Co-receptor tropism is assessed by comparing the amount of luciferase activity produced in each cell type, both in the presence and absence of drug (see FIG. 3B for interpretation of assay results).

Figure 3B:
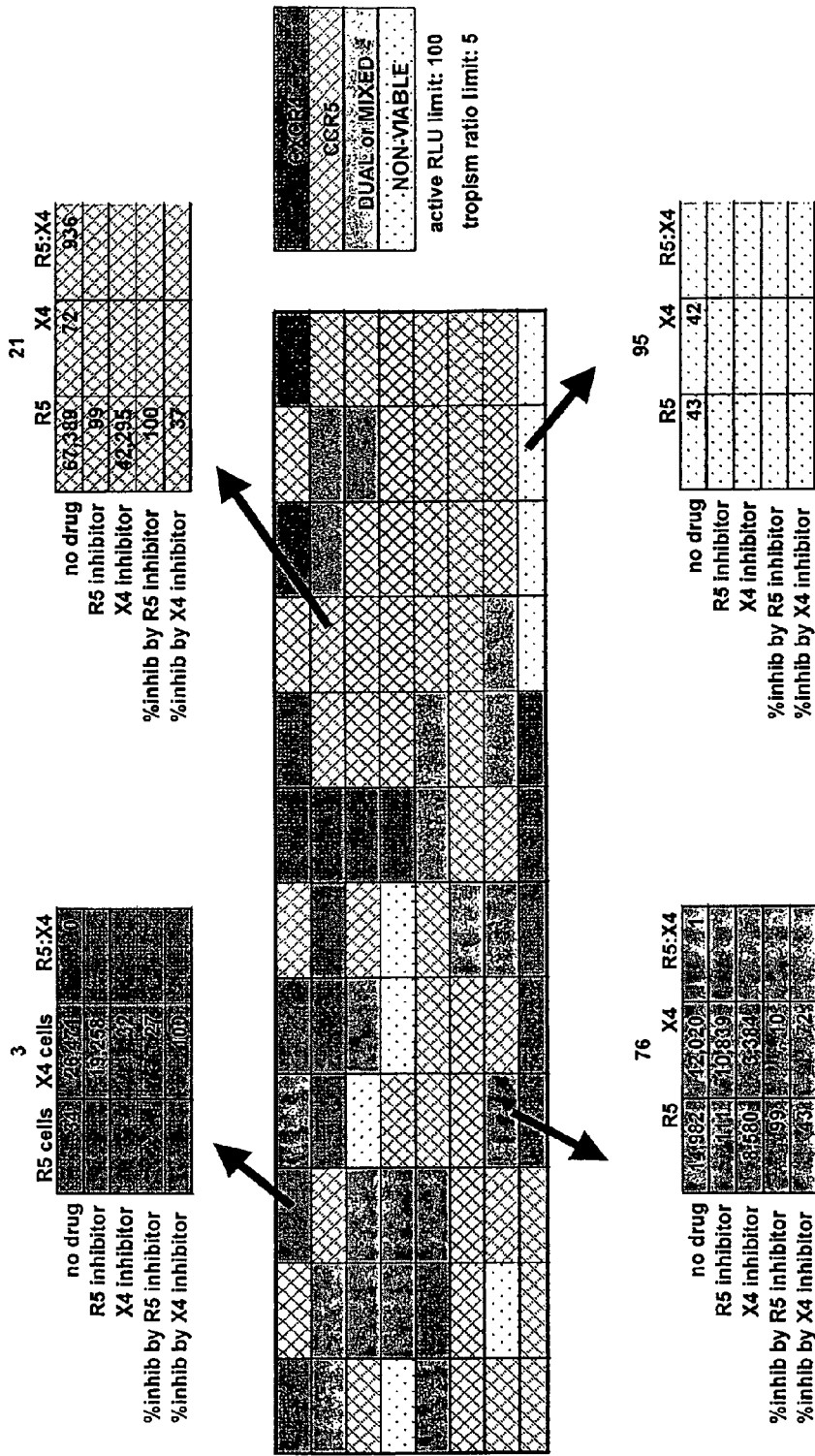

FIG. 3B: Determining co-receptor tropism.

In this figure, the results of the assay are interpreted by comparing the ability of each sample virus to infect (as assessed by the ability to produce luciferase activity) in cells expressing CD4/CCR5 or cells expressing CD4/CXCR4. The ability of a CCR5 or CXCR4 inhibitor to specifically block infection (as assessed by inhibition of luciferase activity) is also evaluated. X4-tropic viruses infect cells expressing CXCR4 but not cells expressing CCR5. Infection of cells expressing CXCR4 is blocked by the CXCR4 inhibitor. R5-tropic viruses infect cells expressing CCR5 but not cells expressing CXCR4. Infection of cells expressing CCR5 is blocked by the CCR5 inhibitor. Infection of cells expressing CCR5 by DM pools is blocked by the CCR5 inhibitor and infection of cells expressing CXCR4 by DM pools is blocked by the CXCR4 inhibitor. Individual clones that infect cells expressing CCR5 and CXCR4 are classified as dual tropic viruses and can be further classified according to their ability to infect the cells expressing CXCR4 and CCR5. Dual tropic viruses that infect cells expressing CCR5 efficiently but enter cells expressing CXCR4 inefficiently are classified as Dual_R. Dual tropic viruses that infect cells expressing CXCR4 efficiently but enter cells expressing CCR5 inefficiently are classified as Dual_X. Non-viable viruses do not replicate in either cells expressing CCR5 or CXCR4.

Figure 4A:
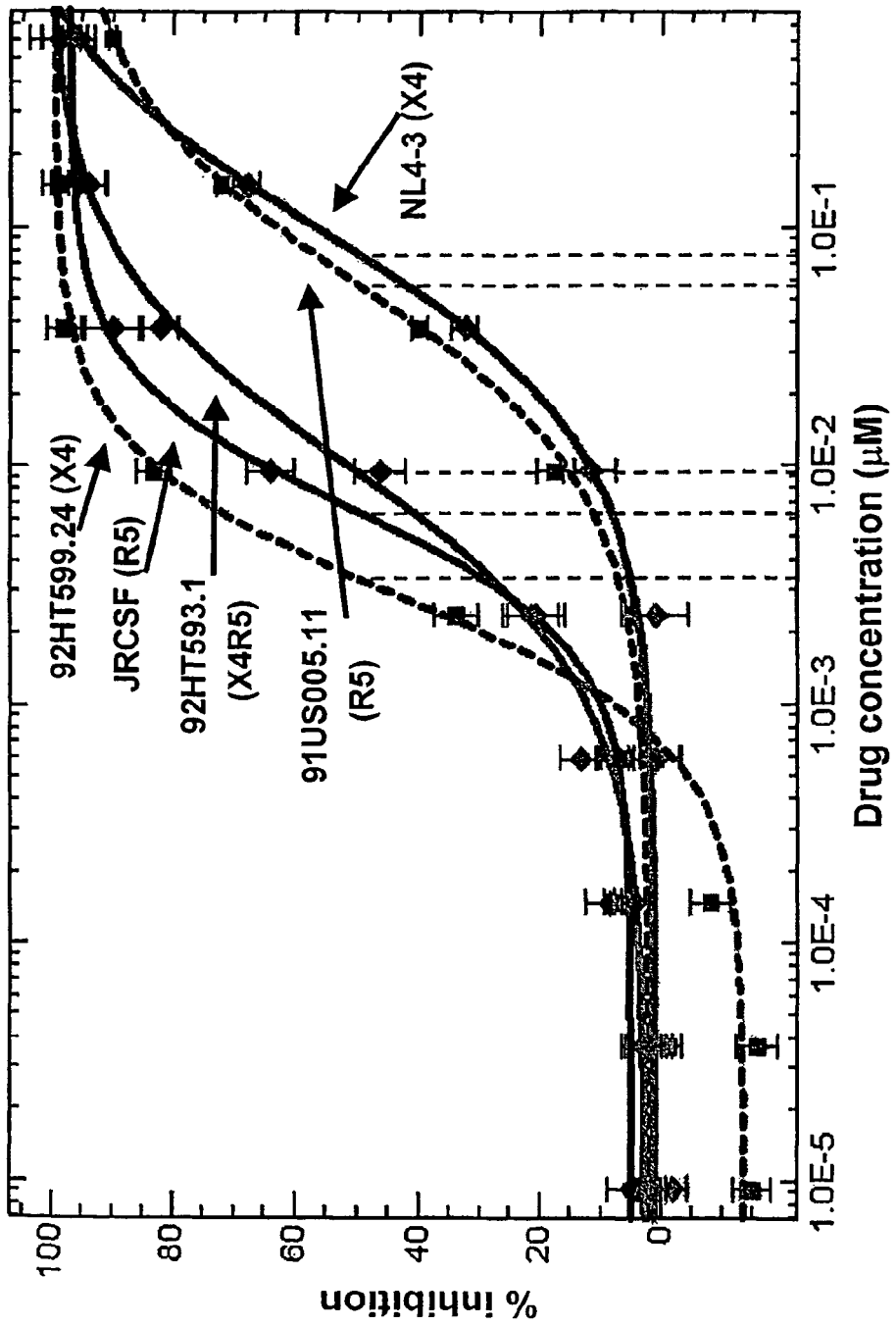

FIG. 4A: Measuring Entry Inhibitor susceptibility: Fusion Inhibitor.

In this figure, susceptibility to the fusion inhibitor T-20 is demonstrated. Cells expressing CD4, CCR5 and CXCR4 were infected in the absence of T-20 and over a wide range of T-20 concentrations x-axis log 10 scale). The percent inhibition of viral replication (y-axis) was determined by comparing the amount of luciferase produced in infected cells in the presence of T-20 to the amount of luciferase produced in the absence of T-20. R5 tropic, X4 tropic and dual tropic viruses were tested. Drug susceptibility is quantified by determining the concentration of T-20 required to inhibit 50% of viral replication ($IC_{50}$, shown as vertical dashed lines). Viruses with lower $IC_{50}$ values are more susceptible to T-20 than viruses with higher $IC_{50}$ values. NL4-3: well-characterized X4 tropic strain, JRCSF: well-characterized R5 tropic strain, 91US005.11: R5 tropic isolate obtained from the NIH AIDS Research and Reference Reagent Program (ARRRP), 92HT593.1: Dual tropic (X4R5) isolate obtained from the NIH ARRRP, and 92HT599.24: X4 tropic isolate obtained from the NIH ARRRP.

Figure 4B:
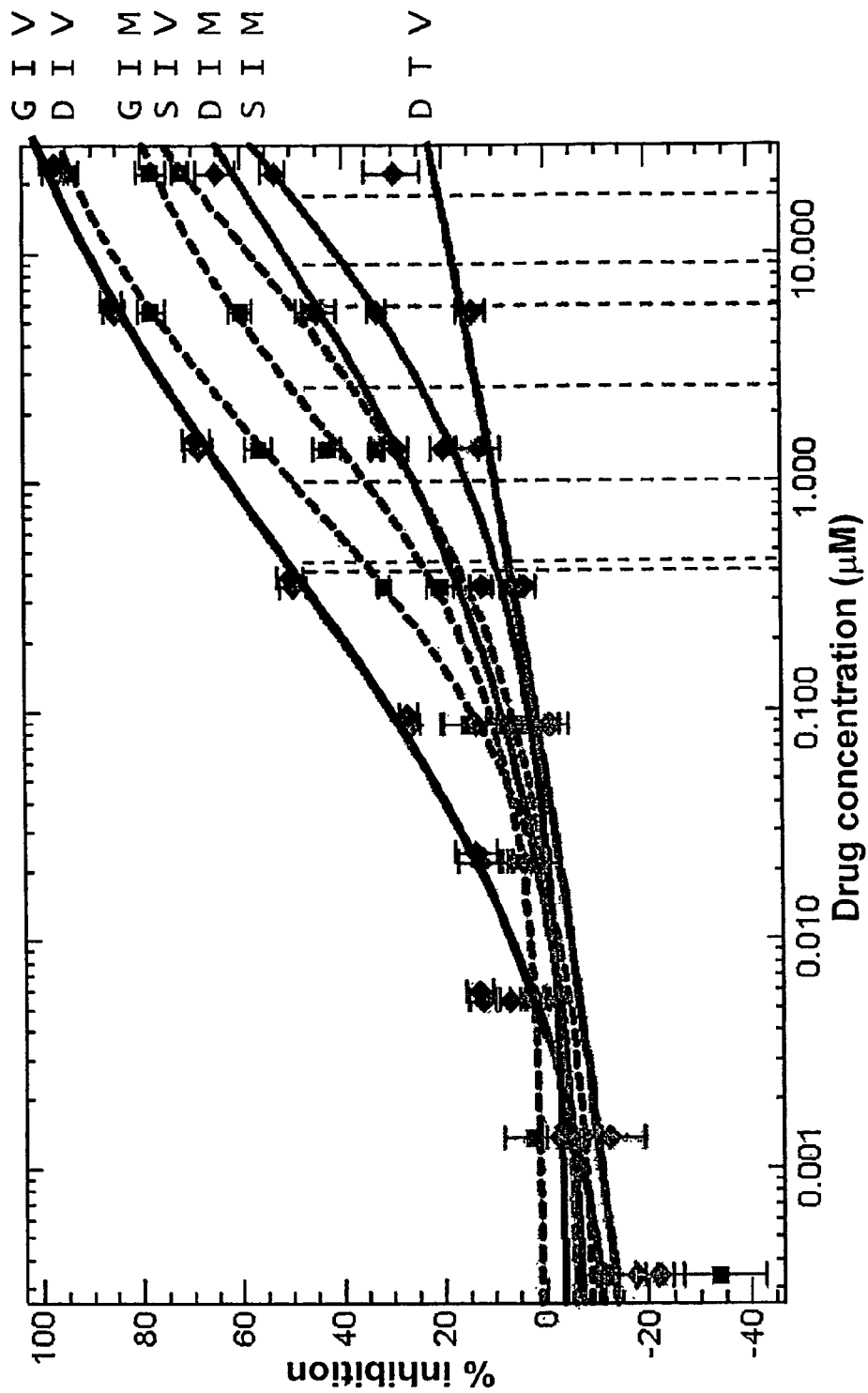

FIG. 4B: Measuring Entry Inhibitor susceptibility: Drug Resistance Mutations.

In this figure, reduced susceptibility to the fusion inhibitor T-20 conferred by specific drug resistance mutations in the gp41 envelope protein is demonstrated. Cells expressing CD4, CCR5 and CXCR4 were infected in the absence of T-20 and over a wide range of T-20 concentrations x-axis log 10 scale). The percent inhibition of viral replication (y-axis) was determined by comparing the amount of luciferase produced in infected cells in the presence of T-20 to the amount of luciferase produced in the absence of T-20. Isogenic viruses containing one or two specific mutations in the gp41 transmembrane envelope, protein were tested (highlighted in red in the figure legend). Drug susceptibility is quantified by determining the concentration of T-20 required to inhibit 50% of viral replication ($IC_{50}$, shown as vertical dashed lines). Viruses with lower $IC_{50}$ values are more susceptible to T-20 than viruses with higher $IC_{50}$ values. No mutation (wildtype sequence): GIV; Single mutations: GIV, DIM, SIV; Double mutations: DIM, SIM, DTV.

Figure 5:
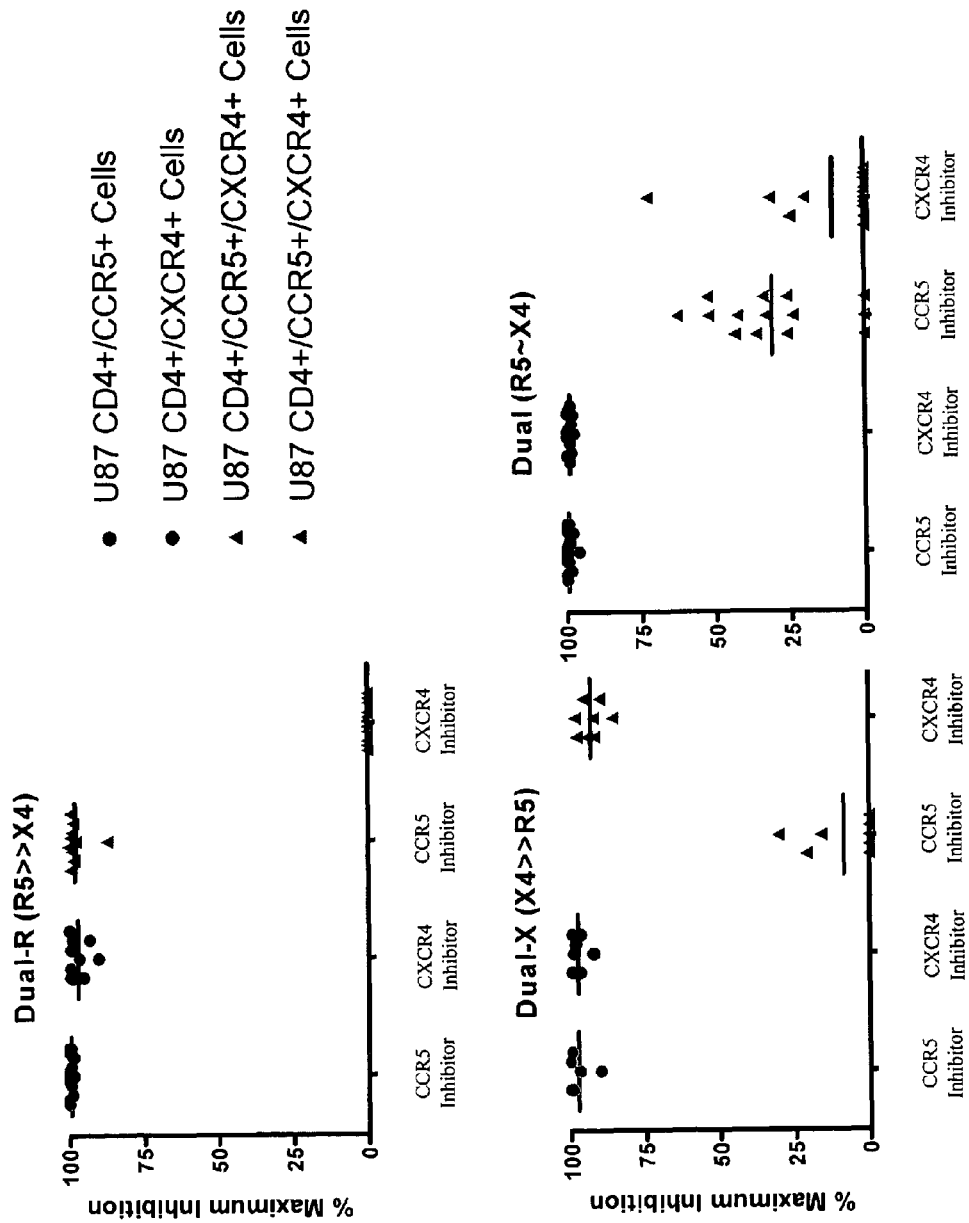

FIG. 5: Different dual subtypes exhibit different patterns of inhibition to co-receptor inhibitors.

FIG. 5 presents a diagram showing different inhibition patters of dual tropic viruses that are Dual_R-tropic, Dual_X-tropic, or Dual tropic when entering cells expressing CD4 and CXCR4, CCR5, or both CXCR4 and CCR5.

Figure 6:
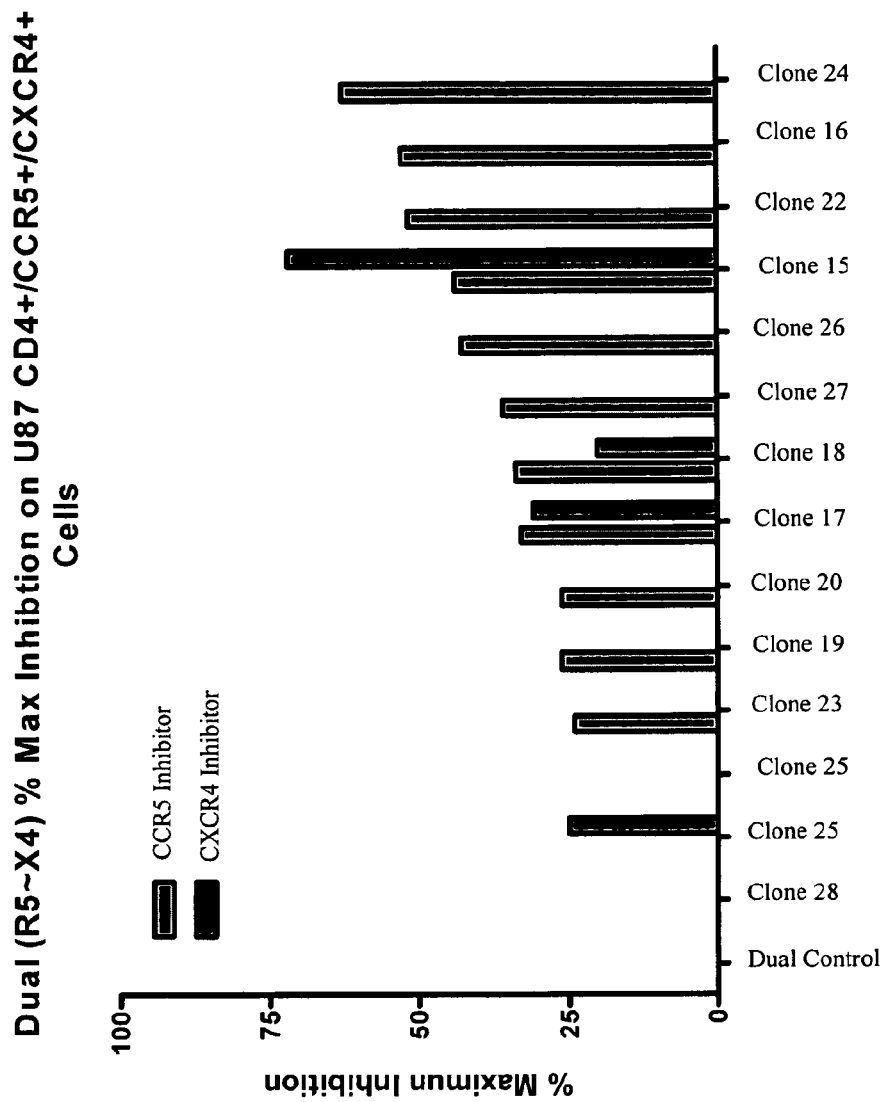

FIG. 6: Dual tropic clones are incompletely inhibited on cells expressing CD4 and CXCR4 and CCR5.

FIG. 6 presents a diagram showing relative inhibition by CCR5 inhibitors and CXCR4 inhibitors of entry to cells expressing CD4 and CXCR4, CD4 and CCR5, or CD4 and both CXCR4 and CCR5.

Figure 7:
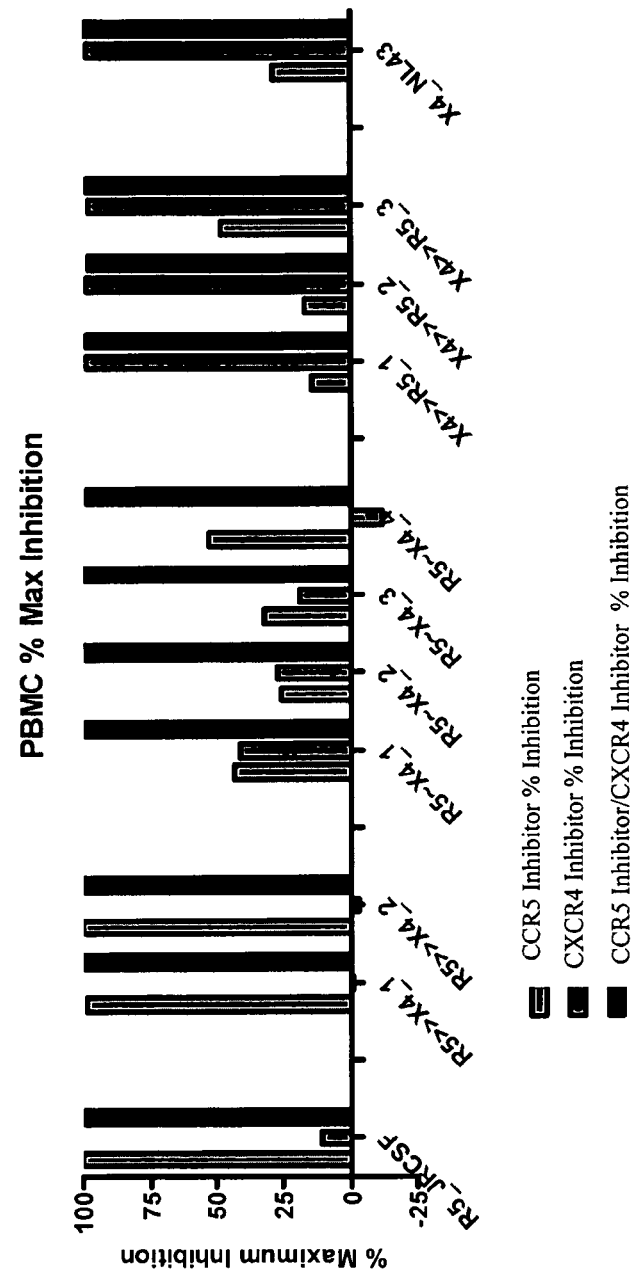

FIG. 7: Infectious clones exhibit similar patterns of inhibition by co-receptor inhibitors on PBMCs.

FIG. 7 presents a diagram showing relative block by CCR5-inhibitors and CXCR4-inhibitors to infection of peripheral blood monocytic cells (PBMCs).

FIG. 8: Suppression of CXCR4-tropic viruses following CXCR4 inhibitor therapy.

FIG. 8 presents a table showing patients expreriencing suppression and non-suppression of CXCR4-tropic viruses following CXCR4-inhibitor therapy.

FIG. 9: Suppression of CXCR4-tropic virus depends on the viral composition at baseline.

FIG. 9 presents a table showing that suppression of CXCR4-tropic virus depends on the relative proportion of CCR5-tropic, CXCR4-tropic, and dual-tropic virus in the viral population at baseline prior to treatment.

4. DEFINITIONS

As used herein, the following terms shall have the following meanings:

A "phenotypic assay" is a functional test that measures a phenotype of a particular virus, such as, for example, HIV, or a population of viruses, such as, for example, the population of HIV infecting a subject. The phenotypes of a virus or virus population that can be measured include, but are not limited to, drug or antibody resistance or susceptibility, replication capacity, infectivity, membrane fusion, virion assembly, virion maturation, virion egress, pathogenesis, or cytopathogenicity.

A "genotypic assay" is an assay that determines a genotype of an organism, a part of an organism, a population of organisms, a gene, a part of a gene, or a population of genes. Typically, a genotypic assay involves determination of the nucleic acid sequence of the relevant gene or genes. Such assays are frequently performed in HIV to establish, for example, whether certain mutations are associated with drug resistance or resistance or altered replication capacity are present. The interpretation of genotypic assay results, based either on rules or algorithms, are often used to predict the phenotype of a virus or virus population, but are themselves not functional assays.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. Exemplary levels of sequence identity include, but are not limited to, 60, 70, 80, 85, 90, 95, 98% or more sequence identity to a given sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. Exemplary levels of sequence homology include, but are not limited to, 60, 70, 80, 85, 90, 95, 98% or more sequence homology to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, *J. Mol. Biol.* 215:403-10 (with special reference to the published default setting, i.e., parameters w=4, t=17) and Altschul et al., 1997, *Nucleic Acids Res.*, 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

A preferred alignment of selected sequences in order to determine "% identity" between two or more sequences, is performed using for example, the CLUSTAL-X program, operated with default parameters, including an open gap penalty of 10.0, an extended gap penalty of 0.1, and a BLOSUM 30 similarity matrix.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (O) Ser (S) and Thr (T).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Ala (A), Gly (G), Ile (I), Leu (L), Met (M) and Val (V).

"Hydrophilic Amino Acid" refers to an amino acid exhibiting a hydrophobicity of less than zero according to the normalized consensus hydrophobicity scale of Eisenberg et al., 1984, *J. Mol. Biol.* 179:125-142. Genetically encoded hydrophilic amino acids include Arg (R), Asn (N), Asp (D), Glu (E), Gln (O), H is (H), Lys (K), Ser (S) and Thr (T).

"Hydrophobic Amino Acid" refers to an amino acid exhibiting a hydrophobicity of greater than zero according to the normalized consensus hydrophobicity scale of Eisenberg et al., 1984, *J. Mol. Biol.* 179:125-142. Genetically encoded hydrophobic amino acids include Ala (A), Gly (G), Ile (I), Leu (L), Met (M), Phe (F), Pro (P), Trp (W), Tyr (Y) and Val (V).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

"Basic Amino Acid" refers to a hydrophilic amino acid having a side chain pK value of greater than 7. Basic amino acids typically have positively charged side chains at physiological pH due to association with a hydrogen ion. Genetically encoded basic amino acids include Arg (R), His (H) and Lys (K).

A "mutation" is a change in an amino acid sequence or in a corresponding nucleic acid sequence relative to a reference nucleic acid or polypeptide. For embodiments of the invention comprising HIV protease or reverse transcriptase, the reference nucleic acid encoding protease, reverse transcriptase, or envelope is the protease, reverse transcriptase, or envelope coding sequence, respectively, present in NL4-3 HIV (GenBank Accession No. AF324493). Likewise, the reference protease, reverse transcriptase, or envelope polypeptide is that encoded by the NL4-3 HIV sequence. Although the amino acid sequence of a peptide can be determined directly by, for example, Edman degradation or mass spectroscopy, more typically, the amino sequence of a peptide is inferred from the nucleotide sequence of a nucleic acid that encodes the peptide. Any method for determining the sequence of a nucleic acid known in the art can be used, for example, Maxam-Gilbert sequencing (Maxam et al., 1980, *Methods in Enzymology* 65:499), dideoxy sequencing (Sanger et al., 1977, *Proc. Natl. Acad. Sci. USA* 74:5463) or hybridization-based approaches (see e.g., Sambrook et al., 2001, *Molecular Cloning: A Laboratory Manual*, Cold Spring Harbor Laboratory, 3$^{rd}$ ed., NY; and Ausubel et al., 1989, *Current Protocols in Molecular Biology*, Greene Publishing Associates and Wiley Interscience, NY).

A "mutant" is a virus, gene or protein having a sequence that has one or more changes relative to a reference virus, gene or protein.

The terms "peptide," "polypeptide" and "protein" are used interchangeably throughout.

The term "wild-type" refers to a viral genotype that does not comprise a mutation known to be associated with drug resistance.

The terms "polynucleotide," "oligonucleotide" and "nucleic acid" are used interchangeably throughout.

A "dual-mixed tropic" population of HIV, as used herein, refers to a population of HIV viruses that collectively have the ability to enter cells expressing CD4 and CCR5 or cells expressing CD4 and CXCR4. Exemplary dual-mixed tropic populations of HIV include, for example, a homogeneous population of dual tropic HIV, a heterogeneous population of HIV that comprises viruses that can enter cells expressing CD4 and CCR5 and viruses that can enter cells expressing CD4 and CXCR4, a heterogeneous population of HIV that comprises viruses that can enter cells expressing CD4 and CCR5 and viruses that can enter cells expressing CD4 and either CCR5 or CXCR4, and the like.

A "homogeneous" population of viruses is a population of viruses whose members have the same or similar phenotype when a statistically significant number of members' phenotypes are assessed. One example of a phenotype according to this definition is a tropism phenotype.

A "heterogeneous" population of viruses is a population of viruses that comprises members having at least two different phenotypes when a statistically significant number of members' phenotypes are assessed. One example of a phenotype according to this definition is a tropism phenotype.

An "R5 tropic" or "CCR5-tropic" virus is a single virus or virus population that can normally enter cells expressing CD4 and CCR5, but do not normally enter cells expressing CD4 and CXCR4.

An "X4 tropic" or "CXCR4-tropic" virus is a single virus or virus population that can normally enter cells expressing CD4 and CXCR4, but do not normally enter cells expressing CD4 and CCR5.

A "dual tropic" or "dual-tropic" virus or viral population is a single virus or virus population that can enter cells expressing CD4 and either CCR5 or CXCR4 that does not have a significantly greater (e.g., 10-fold 100-fold, 1000-fold, or greater) ability to enter cells co-expressing CXCR4 relative to its ability to enter cells co-expressing CCR5, or vice versa.

A Dual_R-tropic virus (also referred to herein as a primarily CCR5-tropic virus) is a single virus that can enter cells expressing CD4 and either CCR5 or CXCR4, but has a significantly greater (e.g., 10-fold, 100-fold, 1000-fold, or greater) ability to enter cells co-expressing CCR5 relative to its ability to enter cells co-expressing CXCR4.

A Dual_X-tropic virus (also referred to herein as a primarily CXCR4-tropic virus) is a single virus that can enter cells expressing CD4 and either CCR5 or CXCR4, but has a significantly greater (e.g., 10-fold, 100-fold, 1000-fold, or greater) ability to enter cells co-expressing CXCR4 relative to its ability to enter cells co-expressing CCR5.

"Substantially more," in the context of the relative phenotypes in a viral population, refers to a proportion of at least about 90% of one phenotype to about 10% or less of one or more other phenotypes. For example, "substantially more" CXCR4-tropic viruses than CCR5 tropic viruses means that, of a total population containing both kinds of viruses, at least about 90% or greater of the viruses are CXCR4 tropic and about 10% or less of the viruses are CCR5 tropic.

"Relatively comparable," in the context of the relative phenotypes in a viral population, refers to a proportion of less than about 90% of one phenotype to 10% or greater of one or more additional phenotypes. For example, "relatively comparable" amounts of CXCR4-tropic and CCR5-tropic viruses means that less than 90% of the total population of HIV is CXCR4-tropic and less than 90% of the total population of HIV is CCR5-tropic.

A "benefit" from a co-receptor inhibitor therapy refers to any desirable clinical or therapeutic endpoint or indicator normally associated with HIV antiviral therapy, and can include, but is not limited to, a reduction in viral load, an inhibition of replication in a particular compartment or target cell type in the body that results in preservation or restoration of that compartment or cell type, a preservation or restoration of compartment or target cell type that results in improved immunologic function (for example, CD4+T-cells) or specific or general health of the patient (for example, suppression of replication in the CNS).

The term "about," as used herein, unless otherwise indicated, refers to a value that is no more than 10% above or below the value being modified by the term. For example, the term "about 5 µg/kg" means a range of from 4.5 µg/kg to 5.5 µg/kg. As another example, "about 1 hour" means a range of from 48 minutes to 72 minutes.

5. DETAILED DESCRIPTION OF THE INVENTION

In certain aspects, the invention provides methods for determining whether a subject infected with a dual-mixed tropic population of human immunodeficiency viruses (HIV) would benefit from CXCR4-inhibitor or CCR5-inhibitor therapy. The methods are useful, for example, to guide therapeutic decisions in treatment subjects infected with HIV, included but not limited to the initiation of treatment or a change in treatment. Change in treatment may be desired, for example, to restore suppression of virus replication (e.g. after treatment failure) or to minimize or eliminate undesirable or toxic side affects (during successful treatment). Other uses of such methods will be apparent to those of skill in the art.

5.1 Determining Viral Tropism Phenotypes

In one aspect, the invention provides a method for determining whether a subject infected with a dual-mixed tropic population of HIV would benefit from CXCR4-inhibitor or CCR5-inhibitor therapy. In such methods, the tropism of the HIV population or the individual HIV of the population can be determined using any method known to one skilled in the art without limitation. In one embodiment, the tropism is determined using a single cell infectivity assay as described in U.S. Pat. Nos. 7,169,551 and 7,097,970 and U.S. Patent Application Publication Nos. 20060183110 and 20060160185. In another embodiment, tropism is determined by performing an infectivity assay using PBMCs in the presence of one or more co-receptor inhibitors.

5.2 Determining Viral Genotypes

Viral genotypes can be detected by utilizing any suitable technique known to one of skill in the art without limitation. Viral DNA or RNA can be used as the starting point for such assay techniques, and may be isolated according to standard procedures which are well known to those of skill in the art.

The determination of specific nucleic acid sequences, such as in a particular region of the env gene, can be accomplished by a variety of methods including, but not limited to, restriction-fragment-length-polymorphism detection based on allele-specific restriction-endonuclease cleavage (Kan and Dozy, 1978, *Lancet* ii:910-912), mismatch-repair detection (Faham and Cox, 1995, *Genome Res* 5:474-482), binding of MutS protein (Wagner et al., 1995, *Nucl Acids Res* 23:3944-3948), denaturing-gradient gel electrophoresis (Fisher et al., 1983, *Proc. Natl. Acad. Sci. U.S.A.* 80:1579-83), single-strand-conformation-polymorphism detection (Orita et al., 1983, *Genomics* 5:874-879), RNAase cleavage at mismatched base-pairs (Myers et al., 1985, *Science* 230:1242), chemical (Cotton et al., 1988, *Proc. Natl. Acad. Sci. U.S.A.* 85:4397-4401) or enzymatic (Youil et al., 1995, *Proc. Natl. Acad. Sci. U.S.A.* 92:87-91) cleavage of heteroduplex DNA, methods based on oligonucleotide-specific primer extension (Syvanen et al., 1990, *Genomics* 8:684-692), genetic bit analysis (Nikiforov et al., 1994, *Nucl Acids Res* 22:4167-4175), oligonucleotide-ligation assay (Landegren et al., 1988, *Science* 241:1077), oligonucleotide-specific ligation chain reaction ("LCR") (Barrany, 1991, *Proc. Natl. Acad. Sci. U.S.A.* 88:189-193), gap-LCR (Abravaya et al., 1995, *Nucl Acids Res* 23:675-682), radioactive or fluorescent DNA sequencing using standard procedures well known in the art, and peptide nucleic acid (PNA) assays (Orum et al., 1993, *Nucl. Acids Res.* 21:5332-5356; Thiede et al., 1996, *Nucl. Acids Res.* 24:983-984).

In addition, viral DNA or RNA may be used in hybridization or amplification assays to detect abnormalities involving gene structure, including point mutations, insertions, deletions and genomic rearrangements. Such assays may include, but are not limited to, Southern analyses (Southern, 1975, *J. Mol. Biol.* 98:503-517), single stranded conformational polymorphism analyses (SSCP) (Orita et al., 1989, *Proc. Natl. Acad. Sci. USA* 86:2766-2770), and PCR analyses (U.S. Pat. Nos. 4,683,202; 4,683,195; 4,800,159; and 4,965,188; PCR Strategies, 1995 Innis et al. (eds.), Academic Press, Inc.).

Such diagnostic methods can involve for example, contacting and incubating the viral nucleic acids with one or more labeled nucleic acid reagents including recombinant DNA molecules, cloned genes or degenerate variants thereof, under conditions favorable for the specific annealing of these reagents to their complementary sequences. Preferably, the lengths of these nucleic acid reagents are at least 15 to 30 nucleotides. After incubation, all non-annealed nucleic acids are removed from the nucleic acid molecule hybrid. The presence of nucleic acids which have hybridized, if any such molecules exist, is then detected. Using such a detection scheme, the nucleic acid from the virus can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining, annealed, labeled nucleic acid reagents is accomplished using standard techniques well-known to those in the art. The gene sequences to which the nucleic acid reagents have annealed can be compared to the annealing pattern expected from a normal gene sequence in order to determine viral env gene sequences.

These techniques can easily be adapted to provide high-throughput methods for determining viral sequences. For example, a gene array from Affymetrix (Affymetrix, Inc., Sunnyvale, Calif.) can be used to rapidly identify genotypes of a large number of individual viruses. Affymetrix gene arrays, and methods of making and using such arrays, are described in, for example, U.S. Pat. Nos. 6,551,784, 6,548,257, 6,505,125, 6,489,114, 6,451,536, 6,410,229, 6,391,550, 6,379,895, 6,355,432, 6,342,355, 6,333,155, 6,308,170, 6,291,183, 6,287,850, 6,261,776, 6,225,625, 6,197,506, 6,168,948, 6,156,501, 6,141,096, 6,040,138, 6,022,963, 5,919,523, 5,837,832, 5,744,305, 5,834,758, and 5,631,734, each of which is hereby incorporated by reference in its entirety.

Alternately, the genotypes of many viruses can be determined simultaneously using or adapting the methods described in Margulies et al., 2005, *Nature* 437:376-380 and in U.S. Pat. Nos. 6,956,114 and 6,902,921.

In addition, Ausubel et al., eds., *Current Protocols in Molecular Biology*, 2002, Vol. 4, Unit 25B, Ch. 22, which is hereby incorporated by reference in its entirety, provides further guidance on construction and use of a gene array for determining the genotypes of a large number of viral isolates. Finally, U.S. Pat. Nos. 6,670,124; 6,617,112; 6,309,823; 6,284,465; and 5,723,320, each of which is incorporated by reference in its entirety, describe related array technologies that can readily be adapted for rapid identification of a large number of viral genotypes by one of skill in the art.

Alternative diagnostic methods for the detection of gene specific nucleic acid molecules may involve their amplification, e.g., by PCR (U.S. Pat. Nos. 4,683,202; 4,683,195; 4,800,159; and 4,965,188; PCR Strategies, 1995 Innis et al. (eds.), Academic Press, Inc.), followed by the detection of the amplified molecules using techniques well known to those of skill in the art. The resulting amplified sequences can be compared to those which would be expected if the nucleic acid being amplified contained only normal copies of the respective gene in order to viral env gene sequences.

Additionally, the nucleic acid can be sequenced by any sequencing method known in the art. For example, the viral DNA can be sequenced by the dideoxy method of Sanger et al., 1977, *Proc. Natl. Acad. Sci. USA* 74:5463, as further described by Messing et al., 1981, *Nuc. Acids Res.* 9:309, or by the method of Maxam et al., 1980, *Methods in Enzymology* 65:499. See also the techniques described in Sambrook et al., 2001, *Molecular Cloning: A Laboratory Manual*, Cold Spring Harbor Laboratory, 3$^{rd}$ ed., NY; and Ausubel et al., 1989, *Current Protocols in Molecular Biology*, Greene Publishing Associates and Wiley Interscience, NY.

Antibodies directed against the viral gene products, i.e., viral proteins or viral peptide fragments can also be used to detect particular envelope protein sequences in the viral proteins. Alternatively, the viral protein or peptide fragments of interest can be sequenced by any sequencing method known in the art in order to yield the amino acid sequence of the protein of interest. An example of such a method is the Edman degradation method which can be used to sequence small proteins or polypeptides. Larger proteins can be initially cleaved by chemical or enzymatic reagents known in the art, for example, cyanogen bromide, hydroxylamine, trypsin or chymotrypsin, and then sequenced by the Edman degradation method.

5.3 Computer-Implemented Methods

In another aspect, the present invention provides computer-implemented methods for performing a method of the invention. In such embodiments, the methods of the invention are adapted to take advantage of the processing power of modern computers. One of skill in the art can readily adapt the methods in such a manner. Such methods generally comprise inputting data regarding a viral population phenotype and/or a virus phenotype into a computer-readable memory, inputting a correlation between the population or virus's phenotype and benefit to a subject for therapy with a co-receptor inhibitor, and determining whether the subject will benefit from such therapy.

In yet another aspect, the invention provides a computer-readable medium that comprises data generated according a method of the invention. In certain embodiments, the computer-readable medium is a random-access memory. In certain embodiments, the computer-readable medium is a fixed disk. In certain embodiments, the computer-readable medium is a floppy disk. In certain embodiments, the computer-readable medium is a portable memory device, such as, e.g., a USB key or an iPod™.

In still another aspect, the invention provides an article of manufacture that comprises computer-readable instructions for performing a method of the invention. In certain embodiments, the article of manufacture is a random-access memory. In certain embodiments, the article of manufacture is a fixed disk. In certain embodiments, the article of manufacture is a floppy disk. In certain embodiments, the article of manufacture is a portable memory device, such as, e.g., a USB key or an iPod™.

In yet another aspect, the invention provides a computer-readable medium that comprises data generated according to method of the invention and computer-readable instructions for performing a method of the invention. In certain embodiments, the computer-readable medium is a random-access memory. In certain embodiments, the computer-readable medium is a fixed disk. In certain embodiments, the computer-readable medium is a floppy disk. In certain embodiments, the computer-readable medium is a portable memory device, such as, e.g., a USB key or an iPod™.

In yet another aspect, the invention provides a computer system that is configured to perform a method of the invention.

5.4 Viruses and Viral Samples

The co-receptor usage phenotypes and susceptibility to co-receptor inhibitor phenotypes of viruses and viral populations can be determined from a viral sample obtained by any means known in the art for obtaining viral samples. Such methods include, but are not limited to, obtaining a viral sample from a human or an animal infected with the virus or obtaining a viral sample from a viral culture. In one embodiment, the viral sample is obtained from a human individual infected with the virus. The viral sample could be obtained from any part of the infected individual's body or any secretion expected to contain the virus. Examples of such parts include, but are not limited to blood, serum, plasma, sputum, lymphatic fluid, semen, vaginal mucus and samples of other bodily fluids. In a preferred embodiment, the sample is a blood, serum or plasma sample.

In another embodiment, the phenotypes are determined from a virus or viral population that can be obtained from a culture. In some embodiments, the culture can be obtained from a laboratory. In other embodiments, the culture can be obtained from a collection, for example, the American Type Culture Collection.

In certain embodiments, the viral or viral population phenotype is determined from a derivative of a virus. In one embodiment, the derivative of the virus is not itself pathogenic. In another embodiment, the derivative of the virus is a plasmid-based system, wherein replication of the plasmid or of a cell transfected with the plasmid is affected by the presence or absence of the selective pressure, such that mutations are selected that increase resistance to the selective pressure. In some embodiments, the derivative of the virus comprises the nucleic acids or proteins of interest, for example, those nucleic acids or proteins to be targeted by an anti-viral treatment. In one embodiment, the genes of interest can be incorporated into a vector. See, e.g., U.S. Pat. Nos. 7,169,551 and 7,097,970 and U.S. Patent Application Publication Nos. 20060183110 and 20060160185, each of which is incorporated herein by reference. In certain embodiments, the genes can be those that encode envelope protein (gp160).

In another embodiment, the intact virus need not be used. Instead, a part of the virus incorporated into a vector can be used. Preferably that part of the virus is used that is targeted by an anti-viral drug.

In another embodiment, the viral or viral population phenotype is determined in a genetically modified virus. The virus can be genetically modified using any method known in the art for genetically modifying a virus. For example, the virus can be grown for a desired number of generations in a laboratory culture. In one embodiment, no selective pressure is applied (i.e., the virus is not subjected to a treatment that favors the replication of viruses with certain characteristics), and new mutations accumulate through random genetic drift. In another embodiment, a selective pressure is applied to the virus as it is grown in culture (i.e., the virus is grown under conditions that favor the replication of viruses having one or more characteristics). In one embodiment, the selective pressure is an anti-viral treatment. Any known anti-viral treatment can be used as the selective pressure.

In certain embodiments, the virus is HIV and the selective pressure is a NNRTI. In another embodiment, the virus is HIV-1 and the selective pressure is a NNRTI. Any NNRTI can be used to apply the selective pressure. Examples of NNRTIs include, but are not limited to, nevirapine, delavirdine and efavirenz. By treating HIV cultured in vitro with a NNRTI, one can select for mutant strains of HIV that have an increased resistance to the NNRTI. The stringency of the selective pressure can be manipulated to increase or decrease the survival of viruses not having the selected-for characteristic.

In other embodiments, the virus is HIV and the selective pressure is a NRTI. In another embodiment, the virus is HIV-1 and the selective pressure is a NRTI. Any NRTI can be used to apply the selective pressure. Examples of NRTIs include, but are not limited to, AZT, ddI, ddC, d4T, 3TC, abacavir, and tenofovir. By treating HIV cultured in vitro with a NRTI, one can select for mutant strains of HIV that have an increased resistance to the NRTI. The stringency of the selective pressure can be manipulated to increase or decrease the survival of viruses not having the selected-for characteristic.

In still other embodiments, the virus is HIV and the selective pressure is a PI. In another embodiment, the virus is HIV-1 and the selective pressure is a PI. Any PI can be used to apply the selective pressure. Examples of PIs include, but are not limited to, saquinavir, ritonavir, indinavir, nelfinavir, amprenavir, lopinavir and atazanavir. By treating HIV cultured in vitro with a PI, one can select for mutant strains of HIV that have an increased resistance to the PI. The stringency of the selective pressure can be manipulated to increase or decrease the survival of viruses not having the selected-for characteristic.

In still other embodiments, the virus is HIV and the selective pressure is an entry inhibitor. In another embodiment, the virus is HIV-1 and the selective pressure is an entry inhibitor. Any entry inhibitor can be used to apply the selective pressure. An example of a entry inhibitor includes, but is not limited to, fusion inhibitors such as, for example, enfuvirtide. Other entry inhibitors include co-receptor inhibitors, such as, for example, AMD3100 (Anormed). Such co-receptor inhibitors can include any compound that interferes with an interaction between HIV and a co-receptor, e.g., CCR5 or CRCX4, without limitation. Still other entry inhibitors include UK-427857 (Pfizer), TNX-355 (Tanox Inc.), AMD-070 (AnorMED), Pro 140 (Progenics), FP-21399 (EMD Lexigen), BMS-488043 (Bristol-Myers Squibb), and GSK-873,140 (GlaxoSmithKline). By treating HIV cultured in vitro with an entry inhibitor, one can select for mutant strains of HIV that have an increased resistance to the entry inhibitor. The stringency of the selective pressure can be manipulated to increase or decrease the survival of viruses not having the selected-for characteristic.

In another aspect, a mutation associated an altered tropism phenotype can be made by mutagenizing a virus, a viral genome, or a part of a viral genome. Any method of mutagenesis known in the art can be used for this purpose. In certain embodiments, the mutagenesis is essentially random. In certain embodiments, the essentially random mutagenesis is performed by exposing the virus, viral genome or part of the viral genome to a mutagenic treatment. In another embodiment, a gene that encodes a viral protein that is the target of an anti-viral therapy is mutagenized. Examples of essentially random mutagenic treatments include, for example, exposure to mutagenic substances (e.g., ethidium bromide, ethylmethanesulphonate, ethyl nitroso urea (ENU) etc.) radiation (e.g., ultraviolet light), the insertion and/or removal of transposable elements (e.g., Tn5, Tn10), or replication in a cell, cell extract, or in vitro replication system that has an increased rate of mutagenesis. See, e.g., Russell et al., 1979, *Proc. Nat. Acad. Sci. USA* 76:5918-5922; Russell, W., 1982, Environmental Mutagens and Carcinogens: Proceedings of the Third International Conference on Environmental Mutagens. One of skill in the art will appreciate that while each of these methods of mutagenesis is essentially random, at a molecular level, each has its own preferred targets.

In another aspect, a viral population or virus phenotype can be determined in an HIV or HIV derivative made using site-directed mutagenesis. Any method of site-directed mutagenesis known in the art can be used (see e.g., Sambrook et al., 2001, *Molecular Cloning: A Laboratory Manual*, Cold Spring Harbor Laboratory, 3rd ed., NY; and Ausubel et al., 1989, *Current Protocols in Molecular Biology*, Greene Publishing Associates and Wiley Interscience, NY). See, e.g., Sarkar and Sommer, 1990, *Biotechniques,* 8:404-407. The site directed mutagenesis can be directed to, e.g., a particular gene or genomic region, a particular part of a gene or genomic region, or one or a few particular nucleotides within a gene or genomic region. In one embodiment, the site directed mutagenesis is directed to a viral genomic region, gene, gene fragment, or nucleotide based on one or more criteria. In one embodiment, a gene or a portion of a gene is subjected to site-directed mutagenesis because it encodes a protein that is known or suspected to be a target of an anti-viral therapy, e.g., the gene encoding the HIV reverse transcriptase. In another embodiment, a portion of a gene, or one or a few nucleotides within a gene, are selected for site-directed mutagenesis. In one embodiment, the nucleotides to be mutagenized encode amino acid residues that are known or suspected to interact with an anti-viral compound. In another embodiment, the nucleotides to be mutagenized encode amino acid residues that are known or suspected to be mutated in viral strains that are resistant or susceptible or hypersusceptible to one or more antiviral agents. In another embodiment, the mutagenized nucleotides encode amino acid residues that are adjacent to or near in the primary sequence of the protein residues known or suspected to interact with an anti-viral compound or known or suspected to be mutated in viral strains that are resistant or susceptible or hypersusceptible to one or more antiviral agents. In another embodiment, the mutagenized nucleotides encode amino acid residues that are adjacent to or near to in the secondary, tertiary or quaternary structure of the protein residues known or suspected to interact with an anti-viral compound or known or suspected to be mutated in viral strains having an altered replication capacity. In another embodiment, the mutagenized nucleotides encode amino acid residues in or near the active site of a protein that is known or suspected to bind to an anti-viral compound.

6. EXAMPLES

The following examples are presented to further illustrate and explain the present invention and should not be taken as limiting in any regard. Certain of these experiments were also described in U.S. Pat. Nos. 7,169,551 and 7,097,970 and U.S. Patent Application Publication Nos. 20060183110 and 20060160185, each of which is incorporated by reference in its entirety.

6.1 Example 1

Measuring Phenotypic Drug Susceptibility to Inhibitors of HIV-1 Entry

This example provides a means and method for accurately and reproducibly measuring susceptibility to inhibitors of HIV-1 attachment and entry (heretofore collectively referred to as entry). Based on this example, the means and method for measuring susceptibility to inhibitors of HIV-1 entry can be adapted to other viruses, including, but not limited to other lentiviruses (e.g. HIV-2), other retroviruses (e.g. HTLV-1 and 2), hepadnaviruses (human hepatitis B virus), flaviviruses (human hepatitis C virus) and herpesviruses human cytomegalovirus). This example further provides a means and method for measuring alterations (increases and decreases) in susceptibility to entry inhibitors.

Measurements of entry inhibitor susceptibility are carried out using adaptations of the means and methods for phenotypic drug susceptibility and resistance tests described in U.S. Pat. No. 5,837,464 (International Publication Number WO 97/27319) which is hereby incorporated by reference.

One vector, an example of the envelope expression vector, (pHIVenv) is designed to express the envelope polyprotein (gp160) encoded by subject derived HIV envelope sequences (FIG. 1). Gp160 is subsequently cleaved by a cellular protease to generate the surface (gp120SU) and transmembrane (gp41™) subunits that comprise the envelope protein on the surface of HIV-1 virus particles. A second vector, an example of the viral expression vector, (either pHIVluc or pHIVlucΔU3) is designed to express genomic and subgenomic viral RNAs and all HIV proteins except the envelope polyprotein (FIGS. 1A-1B).

In this application, patient-derived segment(s) correspond to the coding region (~2.5 KB) of the HIV-1 envelope polyprotein (gp160) and represent either (a) envelope sequences amplified by the reverse transcription-polymerase chain reaction method CRT-PCR) using viral RNA isolated from virus derived from HIV-infected individuals, or (b) envelope sequences derived from molecular clones of HIV-1 that contain specific mutations introduced by site directed mutagenesis of a parental molecular clone (typically NL4-3).

Isolation of viral RNA was performed using standard procedures (e.g. RNAgents Total RNA Isolation System, Promega, Madison Wis. or RNAzo1, Tel-Test, Friendswood, Tex.). The RT-PCR protocol was divided into two steps. A retroviral reverse transcriptase [e.g. Superscript II (Invitrogen, Life Technologies) Moloney MuLV reverse transcriptase (Roche Molecular Systems, Inc., Branchburg, N.J.), or avian myeloblastosis virus (AMV) reverse transcriptase, (Boehringer Mannheim, Indianapolis, Ind.)] was used to copy viral RNA into first strand cDNA. The cDNA was then amplified to high copy number using a thermostable DNA polymerase [e.g. Taq (Roche Molecular Systems, Inc., Branchburg, N.J.), Tth (Roche Molecular Systems, Inc., Branchburg, N.J.), PrimeZyme (isolated from *Thermus brockianus*, Biometra, Gottingen, Germany)] or a combination of thermostable polymerases as described for the performance of "long PCR" (Barnes, W. M., (1994) Proc. Natl. Acad. Sci, USA 91, 2216-2220) [e.g. Expand High Fidelity PCR System (Taq+Pwo), (Boehringer Mannheim. Indianapolis, Ind.) OR GeneAmp XL PCR kit (Tth+ Vent), (Roche Molecular Systems, Inc., Branchburg, N.J.), Advantage-2, (CloneTech).

Oligo-dT was used for reverse transcription of viral RNA into first strand cDNA. Envelope PCR primers, forward primer Xho/Pin and reverse primer Mlu/Xba (Table 3) were used to amplify the patient-derived segments. These primers are designed to amplify the ~2.5 kB envelope gene encoding the gp160 envelope polyprotein, while introducing Xho I and Pin AI recognition sites at the 5' end of the PCR amplification product, and Mlu I and Xba I sites at the 3' end of the PCR amplification product.

Subject derived segments (2.5 kB envelope sequence amplification product) were inserted into HIV-1 envelope expression vectors using restriction endonuclease digestion, DNA ligation and bacterial transformation methods as described in U.S. Pat. No. 5,837,464 (International Publication Number WO 97/27319), with minor adaptations. The ~2.5 kB amplification product was digested with either Xho I or Pin AI at the 5' end and either Mlu I or Xba I at the 3' end. The resulting digestion products were ligated, using DNA ligase, into the 5' Xho I/Pin AI and 3' Mlu I/Xba I sites of modified pCXAS or pCXAT expression vectors. The construction of the pCXAS and pCXAT vectors has been described in U.S. Pat. No. 5,837,464 (International Publication Number WO 97/27319)). Modified pCXAS and pCXAT vectors contain a Pin AI restriction site in addition to the Xho I, MluI and Xba I restriction sites that exist in pCXAS and pCXAT. The Pin AI site was introduced between the Xho I and Mlu I sites by site directed mutagenesis, such that the four sites are located 5' to 3' in the following order; Xho I, Pin AI, Mlu I and Xba I. In a preferred embodiment, the 2.5 kB amplification products were digested with Pin AI and Mlu I and ligated into the 5' Pin AI site and the 3' Mlu I site of the modified pCXAS expression vector. Ligation reaction products were used to transform *E. coli*. Following a 24-36 h incubation period at 30-37° C., the expression vector plasmid DNA was purified from the *E. coli* cultures. To ensure that expression vector preparations adequately represents the HIV quasi-species present in the serum of a given subject, many (>100) independent *E. coli* transformants were pooled and used for the preparations of pHIVenv plasmid DNA. Vectors that are assembled in this manner for the purposes of expressing subject virus derived envelope proteins are collectively referred to as pHIVenv (FIGS. 1 and 3).

The genomic HIV expression vectors pHIVluc and pHIVlucΔU3 are designed to transcribe HIV genomic RNA and subgenomic mRNAs and to express all HIV proteins except the envelope polyprotein (FIG. 1B). In these vectors, a portion of the envelope gene has been deleted to accommodate a functional indicator gene cassette, in this case, "Firefly Luciferase" that is used to monitor the ability of the virus to replicate in the presence or absence of anti-viral drugs. In pHIVlucΔU3, a portion of the 3' U3 region has been deleted to prevent transcription of viral RNAs from the 5' LTR in infected cells.

Susceptibility assays for HIV-1 entry inhibitors were performed using packaging host cells consisting of the human embryonic kidney cell line 293 (Cell Culture Facility, UC San Francisco, SF, CA) and target host cells consisting of a human osteosarcoma (HOS) cell line expressing CD4 (HT4) plus CCR5, and CXCR4, or astrocytoma (U-87) cell lines expressing either CD4 and CCR5 or CD4 and CXCR4.

Drug susceptibility testing was performed using pHIVenv and pHIVluc or pHIV1ucΔU3. Pseudotyped HIV particles containing envelope proteins encoded by the subject derived segment were produced by transfecting a packaging host cell (HEK 293) with resistance test vector DNA. Virus particles were collected (~48 h) after transfection and are used to infect target cells (HT4/CCR5/CXCR4, or U-87/CD4/CXCR4, or U-87/CD4/CCR5) that express HIV receptors (i.e. CD4) and co-receptors (i.e. CXCR4, CCR5). After infection (~72 h) the target cells are lysed and luciferase activity is measured. HIV must complete one round of replication to successfully infect the target host cell and produce luciferase activity. The amount of luciferase activity detected in the infected cells is used as a direct measure of "infectivity" (FIGS. 1 and 2). If for any reason (e.g. lack of the appropriate receptor or co-receptor, inhibitory drug activity, neutralizing antibody binding), the virus is unable to enter the target cell, luciferase activity is diminished. Thus, the assay permits identification of co-receptor usage of the tested virus particles by measuring the ability of the particles to enter cells expressing CD4 and either CCR5 or CXCR4 or both, in the presence or absence of co-receptor inhibitors (FIGS. 3A and 3B).

Drug susceptibility is assessed by comparing the infectivity in the absence of drug to infectivity in the presence of drug. Relative drug susceptibility can be quantified by comparing the susceptibility of the "test" virus to the susceptibility of a well-characterized reference virus (wildtype) derived from a molecular clone of HIV-1, for example NL4-3 or HXB2.

Packaging host cells were seeded in 10-cm-diameter dishes and were transfected one day after plating with pHIVenv and pHIVluc or pHIVlucΔU3. Transfections were performed using a calcium-phosphate co-precipitation procedure. The cell culture media containing the DNA precipitate was replaced with fresh medium, from one to 24 hours, after transfection. Cell culture media containing viral particles was typically harvested 2 days after transfection and was passed through a 0.45-mm filter. Before infection, target cells were plated in cell culture media. Entry inhibitor drugs were typically added to target cells at the time of infection (one day prior to infection on occasion). Typically, 3 days after infection target cells were assayed for luciferase activity using the Steady-Glo reagent (Promega) and a luminometer.

6.2 Example 2

Identifying Envelope Amino Acid Substitutions/Mutations that Alter Susceptibility to Virus Entry Inhibitors This example provides a means and method for identifying mutations in HIV-1 envelope that confer altered, e.g., reduced susceptibility/resistance to virus entry inhibitors. This example also provides a means and method for quantifying the degree of altered, e.g., reduced susceptibility to entry inhibitors conferred by specific envelope mutations.

Envelope sequences derived from subject samples, or individual clones derived from subject samples, or envelope sequences engineered by site directed mutagenesis to contain specific mutations, were tested in the entry assay to quantify drug susceptibility based on a well-characterized reference standard (e.g. NL4-3, HXB2).

In one embodiment, susceptibility to longitudinal subject samples (viruses collected from the same subject at different timepoints) is evaluated. For example, susceptibility to entry inhibitors is measured prior to initiating therapy, before or after changes in drug treatment, or before or after changes in virologic (RNA copy number), immunologic (CD4 T-cells), or clinical (opportunistic infection) markers of disease progression.

6.2.1 Genotypic Analysis of Subject HIV Samples

Envelope sequences representing subject sample pools, or clones derived from subject pools, can be analyzed by any broadly available DNA sequencing methods. In this example, subject HIV sample sequences were determined using viral RNA purification, RT/PCR and dideoxynucleotide chain terminator sequencing chemistry and capillary gel electrophoresis (Applied Biosystems, Foster City, Calif.). Envelope sequences of subject virus pools or clones were compared to reference sequences and other subject samples. The genotypes of the viruses were examined for sequences that are different from the reference or pre-treatment sequence and correlated to differences in entry inhibitor susceptibility, as described below.

6.2.2 Entry Inhibitor Susceptibility of Site Directed Mutants

Genotypic changes that correlate with changes in fitness are evaluated by constructing envelope expression vectors (pHIVenv) containing the specific mutation on a defined, drug susceptible, genetic background (e.g. NL4-3 reference strain). Mutations may be incorporated alone and/or in combination with other mutations that are thought to modulate the entry inhibitor susceptibility. Envelope mutations are introduced into pHIVenv vectors using any of the broadly available methods for site-directed mutagenesis. In certain embodiments the mega-primer PCR method for site-directed mutagenesis is used (Sarkar, G. and Summer, S. S., 1990). A pHIVenv vector containing a specific envelope mutation or group of mutations are tested using the virus entry assay described in Example 1. Drug susceptibility of the virus containing envelope mutations is compared to the drug susceptibility of a genetically defined drug susceptible virus that lacks the specific mutations under evaluation. Observed changes in entry inhibitor susceptibility are attributed to the specific mutations introduced into the pHIVenv vector.

6.3 Example 3

Measuring Susceptibility to Virus Entry Inhibitors to Guide Treatment Decisions This example provides a means and method for using virus entry inhibitor susceptibility to guide the treatment of HIV-1. This example further provides a means and method for using virus entry inhibitor susceptibility to guide the treatment of subjects that have received previous antiretroviral treatment with a virus entry inhibitor. This invention further provides a means and methods for using virus entry inhibitor susceptibility to guide the treatment of subjects that have not received previous treatment with a virus entry inhibitor.

In one embodiment, the susceptibility of subject's viruses to virus entry inhibitors is used to guide the treatment of subjects failing antiretroviral regimens that include one or more virus entry inhibitors. Treatment failure (also referred to as virological failure) is generally defined as partially suppressive antiviral treatment resulting in detectable levels of virus, which is typically measured in the subject plasma. Guidance may include, but is not limited to, (a) clarification of available drug treatment options, (b) selection of more active treatment regimens, (c) clarification of the etiology of rising viral load in treated subjects (i.e. poor adherence, drug resistance), and (d) reduction in the use of inactive and potentially toxic drugs. In this embodiment, resistance test vectors are derived from a subject virus samples and tested for susceptibility to various virus entry inhibitors using the phenotypic virus entry assay. Virus entry inhibitors may include, but are not limited to, fusion inhibitors (e.g. T-20, T-1249), co-receptors antagonists (AMD3100, AMD8664, TAK779, PR0542, and peperidin-lyl butane compounds) and CD4 antagonists (MAb B4). Appropriate treatment decisions are based on the results of the virus entry assay (e.g. see FIG. 4B) and additional relevant laboratory test results and clinical information.

In another embodiment, the susceptibility of subject's viruses to virus entry inhibitors is used to guide the treatment of subjects that have not been previously treated with antiretroviral regimens that include one or more virus entry inhibitors. Guidance may include, but is not limited to, (a) clarification of available drug treatment options, (b) selection of more active treatment regimens, (c) clarification of the baseline susceptibility to virus entry inhibitors, and (d) reduction in the use of inactive and potentially toxic drugs. Determining baseline susceptibility of virus entry inhibitors in treatment naive subjects is important for two reasons. First, the natural susceptibility of viruses to entry inhibitors can vary widely (e.g. see FIG. 4A). Second, the increased use of virus entry inhibitors will undoubtedly result in the generation of drug resistant variants that can be transmitted to newly infected individuals. In this embodiment, resistance test vectors are derived from a subject virus samples and tested for susceptibility to various virus entry inhibitors using the phenotypic virus entry assay. Virus entry inhibitors may include, but are not limited to, fusion inhibitors (e.g. T-20, T-1249), co-receptor antagonists (e.g. AMD3100, AMD8664, TAK-355, PR0542, and peperidin-lyl butane compounds) and CD4 antagonists (MAb 5A8). Appropriate treatment decisions are based on the results of the virus entry assay and additional relevant laboratory test results and clinical information.

6.4 Example 4

Exploring the Effects of Co-Receptor Inhibitors on Homogeneous Viral Populations This example describes the results of experiments designed to assess the effects of co-receptor inhibitors on homogeneous populations of dual-tropic viruses. First, 35 gp160 envelope genes derived from different patient samples that were originally identified as dual-tropic were cloned into an expression vector as described in Example 1. Tropism of pseudotyped virus was determined by measuring luciferase activity (relative light units, RLU) following infection of U87/CD4+CCR5+ or U87/CD4+CXCR4+ cells as described above. Inhibition of infection by small molecule CCR5- (Merck) and CXCR4- (AMD3100; AnorMED) inhibitors was examined on U87/CD4+CCR5+CXCR4+ cells, U87/CD4+CXCR4+ cells, and U87/CD4+CCR5+ cells. A subset of the envelope genes were also inserted into an NL4-3 infectious clone and evaluated for their ability to infect PBMCs in the presence of the CCR5- or CXCR4- inhibitors.

Results from the first set of experiments showing tropism of the 35 individual pseudotyped viruses are presented in Table 4, immediately below. In Table 4, the individual clones have been sorted into clones that are primarily CCR5-tropic (shown as R5>>x4 in the table; also referred to herein as Dual_R clones), clones that are dual tropic (shown as R5~X4; also referred to as Dual clones) and clones that are primarily CXCR4-tropic (shown as X4>>R5; also referred to as Dual_X clones).

TABLE 4

| Sample | Dual Type | Normalized RLUs | | |
|---|---|---|---|---|
| | | U87 CCR5+ | U87 CXCR4+ | U87 CCR5+/CXCR4+ |
| JRCSF | R5 | 976,598 | 110 | 1,230,709 |
| Clone 1 | R5 >> X4 | 11,720 | 762 | 8,691 |
| Clone 2 | R5 >> X4 | 572,726 | 2,563 | 459,781 |
| Clone 3 | R5 >> X4 | 627,660 | 1,005 | 396,022 |
| Clone 4 | R5 >> X4 | 736,225 | 17,092 | 762,260 |
| Clone 5 | R5 >> X4 | 885,752 | 14,650 | 693,807 |
| Clone 6 | R5 >> X4 | 961,696 | 199 | 535,129 |
| Clone 7 | R5 >> X4 | 997,251 | 3,502 | 790,073 |
| Clone 8 | R5 >> X4 | 1,082,548 | 4,194 | 1,023,988 |
| Clone 9 | R5 >> X4 | 1,082,628 | 2,328 | 1,075,651 |
| Clone 10 | R5 >> X4 | 1,096,117 | 11,969 | 1,106,647 |
| Clone 11 | R5 >> X4 | 1,116,961 | 1,317 | 821,801 |
| Clone 12 | R5 >> X4 | 1,655,718 | 4,380 | 2,695,407 |
| Clone 13 | | | | |
| Clone 14 | R5~X4 | 203,669 | 177,006 | 241,521 |
| Clone 15 | R5~X4 | 5,552 | 6,471 | 19,785 |
| Clone 16 | R5~X4 | 36,172 | 20,792 | 23,688 |
| Clone 17 | R5~X4 | 43,106 | 97,388 | 57,455 |
| Clone 18 | R5~X4 | 44,826 | 134,845 | 94,003 |
| Clone 19 | R5~X4 | 75,845 | 31,952 | 41,526 |
| Clone 20 | R5~X4 | 114,542 | 85,460 | 100,596 |
| Clone 21 | R5~X4 | 244,734 | 304,576 | 419,322 |
| Clone 22 | R5~X4 | 247,316 | 117,635 | 182,245 |
| Clone 23 | R5~X4 | 369,291 | 345,867 | 414,392 |
| Clone 24 | R5~X4 | 389,392 | 205,340 | 322,182 |
| Clone 25 | R5~X4 | 472,975 | 635,726 | 843,164 |
| Clone 26 | R5~X4 | 707,184 | 435,623 | 499,922 |
| Clone 27 | R5~X4 | 827,294 | 437,614 | 484,149 |
| Clone 28 | R5~X4 | 1,429,209 | 1,601,696 | 1,816,470 |
| Clone 29 | | | | |
| Clone 30 | X4 >> R5 | 256 | 9,210 | 11,700 |
| Clone 31 | X4 >> R5 | 824 | 71,954 | 87,239 |
| Clone 32 | X4 >> R5 | 2,638 | 74,893 | 48,381 |
| Clone 33 | X4 >> R5 | 513 | 399,563 | 468,71 |
| Clone 34 | X4 >> R5 | 28,427 | 655,790 | 433,996 |
| Clone 35 | X4 >> R5 | 11,153 | 689,002 | 712,325 |
| Clone 36 | X4 >> R5 | 613 | 727,745 | 614,032 |
| Clone 37 | X4 >> R5 | 9,105 | 811,378 | 636,845 |
| NL43 | X4 | 65 | 602,816 | 724,602 |

Next, inhibition patterns for clones representing primarily CCR5-tropic, dual tropic, and primarily CXCR4-tropic viruses were determined. In these experiments, the ability of psuedotyped viruses to enter cells expressing CD4 and either or both of CCR5 and/or CXCR4 were tested in the presence of the CCR5 inhibitor or the CXCR4 inhibitor. Results from this experiment are presented as FIG. 5.

As shown in FIG. 5, entry of primarily CCR5-tropic viruses into CCR5-expressing and CCR5- and CXCR4-expressing cells was inhibited by the CCR5-inhibitor. Entry of such viruses into cells expressing CCR5 and CXCR4 was not inhibited by the CXCR4-inhibitor. Similarly, entry of primarily CXCR4-tropic viruses into CXCR4-expressing and CCR5- and CXCR4-expressing cells was inhibited by the CXCR4 inhibitor, but entry of such viruses into cells expressing both CXCR4 and CCR5 was not completely inhibited by the CCR5-inhibitor. Entry of dual tropic viruses into cells expressing only CXCR4 or CCR5 could be completely inhibited by the appropriate co-receptor inhibitor, but neither could completely inhibit entry of such viruses into cells expressing both co-receptors. Distribution of the percentage of inhibition for the individual dual tropic clones is shown as FIG. 6.

Taken together, these data indicate that entry of viruses that are primarily CCR5 tropic into cells expressing both CXCR4 and CCR5 can be effectively inhibited with CCR5 inhibitors, notwithstanding the viruses' weak ability to enter cells expressing CXCR4. Similarly, entry of viruses that are primarily CXCR4-tropic into cells expressing both CXCR4 and CCR5 can be effectively inhibited with CXCR4 inhibitors, notwithstanding the viruses' weak ability to enter cells expressing CXCR4.

To confirm that the entry phenotypes observed for the pseudotyped viral particles conforms to the phenotypes of fully replication competent virus, a subset of the envelope genes were inserted into an NL4-3 infectious clone and evaluated for their ability to infect PBMCs in the presence of the CCR5-inhibitor or AMD3100. Results from this experiment are presented in Table 5, below and presented graphically in FIG. 7.

TABLE 5

| Clone ID | Tropism Subtype | | CCR5-inhibitor % inhibition | AMD % inhibition | the CCR5-inhibitor/ AMD % inhibition |
|---|---|---|---|---|---|
| JRCSF | R5_JRCSF | R5 | 100% | 11% | 100% |
| Clone 4 | R5>>X4_1 | R5>>X4 | 99% | −1% | 100% |
| Clone 11 | R5>>X4_2 | R5>>X4 | 100% | −3% | 100% |
| Clone 26 | R5~X4_1 | R5~X4 | 43% | 41% | 100% |
| Clone 25 | R5~X4_2 | R5~X4 | 26% | 27% | 100% |
| Clone 28 | R5~X4_3 | R5~X4 | 32% | 19% | 100% |
| Clone 22 | R5~X4_4 | R5~X4 | 53% | −12% | 99% |
| Clone 34 | X4>>R5_1 | X4>>R5 | 14% | 99% | 99% |
| Clone 33 | X4>>R5_2 | X4>>R5 | 17% | 99% | 98% |
| Clone 31 | X4>>R5_3 | X4>>R5 | 48% | 98% | 99% |
| NL43 | X4_NL43 | X4 | 29% | 99% | 100% |

As shown in FIG. 7 and Table 5, the results observed for the fully replication competent viruses were consistent with those obtained from pseudotyped viral particles: entry of Dual_R-tropic viruses could be substantially inhibited by the CCR5 inhibitor, while entry of Dual_X-tropic viruses could be substantially inhibited by the CXCR4 inhibitor. Entry of the dual-tropic viruses could be partially inhibited with either the CCR5-inhibitor or the CXCR4-inhibitor, but could not be completely inhibited.

Finally, it was observed that individual patients were infected with clones of differing subtypes; for example, one subject (from which clones 9, 36, and 37 were isolated) was infected with one primarily CCR5-tropic viral subpopulation and at least one primarily CXCR4-tropic viral subpopulation (Table 4). Accordingly, the relative contributions of different subpopulations to entry was assessed in another set of experiments as described below.

6.5 Example 5

Analysis of Suppression of Primarily CXCR4-Tropic Viruses in Heterogeneous Populations Infecting Patients This example describes the results of experiments performed to assess suppression of dual-tropic HIV-1 variants by the CXCR4 inhibitor AMD3100 patients over time. In brief, the results of these experiments indicate that such suppression is associated with efficiency of CXCR4 use and clonal composition of the baseline virus population.

First, samples from 26 subjects administered AMD3100 for 10 days were obtained prior to therapy and on day 11 following the 10 days of therapy. Co-receptor tropism of the viral populations from both sets of samples were then determined according to Example 1. The results of the population analysis were originally published in Hendrix et al., 2004, *J Acquir Immune Defic Syndr.* 37(2):1253-62.

To further characterize these populations, individual clones from the patients identified as infected with dual-tropic viral populations were subjected to further analysis as described hereinafter. First, patients were classified by the response of the patient virus to the CXCR4 inhibitor into patients that experienced suppression of CXCR4-tropic viruses as a relative proportion of the population (Suppressors) and patients that did not experience suppression of CXCR4-tropic viruses (Non-suppressors). These classifications are shown in FIG. 8.

To begin to assess viral populations of the patients that experienced suppression versus the patients that did not, the tropism phenotypes of 20-50 individual functional envelope clones from each of the patients identified as DM (dual/mixed)-tropic were determined according to Example 1, and the percentage of CCR5-tropic, CXCR4-tropic, or dual-tropic clones before and after therapy were determined. Results from this analysis are presented in FIG. 9.

These results indicate that suppression of CXCR4-tropic virus depended on the viral composition at baseline. Populations comprising 100% dual viruses, e.g., a homogeneous population of dual-tropic viruses, were not suppressed by 10 days of AMD3100 therapy, while populations containing mixtures of CCR5-tropic and CXCR4-tropic or dual-tropic viruses experienced suppression. That is, following treatment with AMD3100, in subjects with mixed populations, entry into cells using the CXCR4 coreceptor was efficiently blocked while entry using the CCR5 coreceptor was unaffected. This led to substantial shifts of tropism away from CXCR4-tropic viruses and towards CCR5-tropic viruses in these subjects.

7. REFERENCES

Adachi, A., H. E. Gendelman, S. Koenig, T. Folks, R. Caney, A. Rabson, and M. A. Martin. 1986. Production of Acquired Immunodeficiency Syndrome-associated Retrovirus in Human and Nonhuman Cells Transfected with an Infectious Molecular Clone. J. Virol. 59:284-291.

Alkhatib, G., C. Combadiere, C. C. Broder, Y. Feng, P. E. Kennedy, P. M. Murphy, and E. A. Berger. 1996. CC CKR5: A Rantes, MIP-1alpha, MIP-1 Beta Receptor as a Fusion Cofactor for Macrophage-tropic HIV-1. Science 272:1955-8.

Allaway G. P., Ryder A. M., Beaudry G. A., and Maddon P. J. 1993. Synergistic Inhibition of HIV-1 Envelope-Mediated Cell Fusion by CD4-based Molecules in Combination with Antibodies to Gp120 or Gp41. Aids Res. Hum. Retroviruses 9:581-7.

Baba, M., O, Nishimura, N. Kanzaki, M. Okamoto, H. Sawada, Y. Iizawa, M. Shiraishi, Y. Aramaki, K. Okonogi, Y. Ogawa, K. Meguro, and M. Fujino. 1999. A Small-molecule, Nonpeptide CCR5 Antagonist with Highly Potent and Selective Anti-hiv-1 Activity. Proc. Natl. Acad. Sci. USA 96:5698-703.

Baxter, J., D. Mayers, D. Wentworth, J. Neaton, and T. Merigan. 1999. A Pilot Study of the Short-term Effects of Antiretroviral Management Based on Plasma Genotypic Antiretroviral Resistance Testing (Gart) in Subjects Failing Antiretroviral Therapy. Presented at the 6th Conference on Retroviruses and Opportunistic Infections. Chicago, Ill.

Bernard P., Kezdy K. e., Van Melderen L., Steyaert J., Wyns L., Pato M. L., Higgins P. N., and Couturier M. 1993. The F Plasmid CcdB protein Induces Efficient ATP-dependent Dna Cleavage by Gyrase. J. Mol. Biol. 23:534-41.

Bernard, P. and Couturier, M. 1992. Cell Killing by the F Plasmid Ccdb protein Involves Poisoning of DNAtopoisomerase II Complexes. J. Mol. Bio. 226:735-45.

Bleul, C. C., M. Farzan, H. Choe, C. Parolin, I. Clark-Lewis, J. Sodroski, and T. A. Springer. 1996. The Lymphocyte Chemoattractant Sdf-1 Is a Ligand for Lestr/fusin and Blocks Hiv-1 Entry. Nature 382:829-33.

Bridger G. J, Skerlj R. T., Padmanabhan S., Martellucci S. A., Henson G. W., Struyf S., Witvrouw M., Schols D., and De Clercq E. 1999. Synthesis and Structure-activity Relationships of Phenylenebis(methylene)-linked Bis-azamacrocycles That Inhibit HIV-1 and HIV-2 Replication by Antagonism of the Chemokine Receptor CXCR4. J. Med. Chem. 42:3971-81.

Carpenter, C. J., Cooper D. A., Fischl, M. A., Gatell J. M., Gazzard B. G., Hammer S. M., Hirsch M. S., Jacobsen D. M., Katzenstein D. A., Montaner J. S., Richman D., Saag M. S., Schechter M., Schooley R. T., Thompson M. A., Vello S., Yeni P. G., and Volberding P. A. 2000. Antiretroviral Therapy in Adults. JAMA 283:381-89.

CDC (Centers for Disease Control and Prevention). HIV/AIDS Surveillance Report, 1999; 11(no. 1).

Coffin, J. M. 1995. HIV Population Dynamics in Vivo: Implications for Genetic Variation, Pathogenesis, and Therapy. Science 267:483-489.

DHHS (Department of Health and Human Services). Henry Kaiser Family Foundation: Guidelines for the Use of Antiretrovirals Agents in HIV-infected Adults and Adolescents. (Jan. 28, 2000).

Gerdes, K., L. K. Poulsen. T. Thisted, A. K. Nielson, J. Martinussen, and P. H. Andreasen. 1990. The Hok Killer Gene Family in Gram-negative Bacteria. The New Biologist: 2:946-956.

Hertogs, K., M. P. De Béthune, V. Miller, T. Ivens, P. Schel, A. V. Cauwenberge, C. Van Den Eynde, V. Van Gerwen, H. Azijn, M. Van Houtte, F. Peeters, S. Staszewski, M. Conant, S. Bloor, S. Kemp, B. Larder, and R. Pauwels. 1998. A Rapid Method for Simultaneous Detection of Phenotypic Resistance to Inhibitors of protease and Reverse Transcriptase in Recombinant Human Immunodeficiency Virus Type 1 Isolates from Subjects Treated with Antiretroviral Drugs. Antimicrob. Agents Chemother. 42:269-276.

Hwang, J.-j., L. Li, W. f. Anderson. 1997. A Conditional Self-inactivating Retrovirus Vector That Uses a Tetracycline-responsive Expression System. J. Virol. 71: 7128-7131.

Japour, A. J., D. L. Mayers, V. A. Johnson, D. R. Kuritzkes, L. A. Beckett, J. M. Arduino, J. Lane, B. R. J., P. S. Reichelderfer, R. T. D-aquila, C. S. Crumpacker, T. R.-S. Group, T.A.C.T. Group, and V. C.R.W. Group. 1993. Standardized Peripheral Blood Mononuclear Cell Culture Assay for Determination of Drug Susceptibilities of Clinical Human Immunodefiency Virus Type 1 Isolates. Antimicrob. Agents Chemother. 37:1095-1101.

Judice J. K., Tom J. Y., Huang W., Wrin T., Vennari J., Petropoulos C. J., and Mcdowell R. S. 1997. Inhibition HIV Type 1 Infectivity by Constrained Alphahelical Peptides: Implications for the Viral Fusion Mechanism. Proc. Natl. Acad. Sci. USA 94:13426-30.

Kilby J M, Hopkins S, Venetta Tm, Dimassimo B, Cloud Ga, Lee Jy, Alldrdge L, Hunter E, Lambert D, Bolognesi D, Matthews T, Johnson Mr. Nowak Ma, Shaw Gm, and Saag Ms. 1998. Potent Suppression of HIV-1 Replication in Humans by T-20, a Peptide Inhibitor of Gp41-mediated Virus Entry. *Nat. Med.* 4:1302-7.

Mascola, J. R., G. Stiegler, T. C. Vancott, H. Katinger, C. B. Carpenter, C. E. Hanson, H. Beary, D. Hayes, S. S. Frankel, D. L. Birx, and M. G. Lewis. 2000. Protection of Macaques Against Vaginal Transmission of a Pathogenic HIV-1/siv Chimeric Virus by Passive Infusion of Neutralizing Antibodies. Nature Med. 6:207-210.

Miyoshi, H., B. Ulrike, M. Takahashi, F. H. Gage, and I. M. Verma. 1998. Development of a Self-inactivating Lentivirus Vector. J. Virol. 72:8150-5157.

Naviaux, R. K., E. Costanzi, M. Haas, and I. M. Verma. 1996. The Pcl Vector System: Rapid production of Helperfree, High-titer, Recombinant Retroviruses. J. Virol. 70: 5701-5705.

Petropoulos, C. J., N. T. Parkin, K. L. Limoli, Y. S. Lie, T. Wrin, W. Huang, H. Tian, D. Smith, G. A. Winslow, D. Capon and J. M. Whitcomb. 2000. A Novel Phenotypic Drug Susceptibility Assay for HIV-1. Antimicrob. Agents & Chem. 44:920-928.

Phrma (Pharmaceutical Research and Manufacturers of America). New Medicines in Development for Aids 1999.

Piketty, C., E. Race, P. Castiel, L. Belec, G. Peytavin, A. si-mohamed, G. Gonzalez-canali, L. Weiss, F. Clavel, and M. Kazatchkine. 1999. Efficacy of a Five-drug Combination Including Ritonavir, Saquinavir and Efavirenz in Subjects Who Failed on a Conventional Triple-drug Regimen: Phenotypic Resistance to protease Inhibitors predicts Outcome of Therapy. Aids: 13:f71-f77.

Porter, C. C., K. V. Lukacs, G. Box, Y. Takeuchi, and M. K. L. Collins. 1998. Cationic Liposomes Enhance the Rate of Transduction by a Recombinant Retroviral Vector in Vitro and in Vivo. J. Virol. 72:4832-4840.

Reimann K. A., Cate R. L., Wu Y., Palmer L., Olson D., Waite B. C., Letvin N. L., and Burkly L. C. 1995. In Vivo Administration of CD4-specific Monoclonal Antibody: Effect on provirus Load in Rhesus Monkeys Chronically Infected with the Simian Immunodeficiency Virus of Macaques. *Aids Res. Hum. Retroviruses* 11:517-25.

Retroviruses. Coffin, J., S. Hughes, H. Varmus (Eds). 1997. Cold Spring Harbor Laboratory Press, Cold Spring Harbor, N.Y.

Richman, D. 1998. Nailing down Another HIV Target. Nature Med. 4:1232-1233.

Rimsky, L. T., D. C. Shugars, and T. J. Matthews. 1998. Determinants of Human Immunodeficiency Virus Type 1 Resistance to Gp41-derived Inhibitory Peptides. J. Virol. 72:986-993.

Rodriguez-Rosado, R., Briones, C. and Soriano, V. 1999. Introduction of HIV Drug-resistance Testing in Clinical Practice. Aids 13:1007-1014.

Schinazi, R. F., Larder, B. A., and Mellors, J. W. 1999. Mutations in Retroviral Genes Associated with Drug Resistance. Intl. Antiviral News: 7:46-49.

Shi C., and J. W. Mellors. 1997. A Recombinant Retroviral System for Rapid in Vivo Analysis of Human Immunodefiency Virus Type 1 Susceptibility to Reverse Transcriptase Inhibitors. Antimicrob. Agents Chemother 41:2781-2785.

Schurmann D et al. SCH D: antiviral activity of a CCR5 receptor antagonist. Eleventh Conference on Retroviruses and Opportunistic Infections, San Francisco, abstract 140LB, 2004.

Stephenson, J. 1999. New Class of Anti-HIV Drugs. Jama 282:1994.

Who, Unaids/World Health Organization. Report: Aids Epidemic Update: December 1999.

Wild, C., T. Oak, C. Mcdanal, D. Bolognesi, and T. Matthews. 1992. A Synthetic Peptide Inhibitor of HIV Replication: Correlation Between Solution Structure and Viral Inhibition. Proc. Natl. Acad. Sci. USA 89:10537-10541.

Zennou, V., F. Mammamo, S. Paulous, D. Mathez, and F. Calvel. 1998. Loss of Viral Fitness Associated with Multiple Gag and Gag-pol processing Defects in Human Immunodefiency Virus Type 1 Variants Selected for Resistance to Protease Inhibitors in vivo. J. Virol: 72:3300-06.

Ziermann, R., K. Limoli, K. Das, E. Arnold, C. J. Petropoulos, and N. T. Parkin. 2000. A Mutation in HIV-1 Protease, N88s, That Causes in Vitro Hypersensitivity to Amprenavir. J. Virol. 74:4414-4419.

What is claimed is:

1. A method for determining whether a subject infected with a dual-mixed tropic population of human immunodeficiency viruses (HIV) would benefit from CXCR4-inhibitor or CCR5-inhibitor therapy, comprising:
   a. determining whether the population is a homogeneous dual-mixed tropic or heterogeneous population by contacting a viral particle with a cell; wherein the viral particle or the cell comprises an indicator gene, the expression of which is dependent upon the entry of the viral particle into the cell; and wherein if the population is a homogeneous dual-mixed tropic population, step b but not step c or d of the method is performed, and wherein if the population is a heterogeneous population, step c and d but not step b of the method are performed;
   b. determining that the subject would benefit from CCR5-inhibitor therapy if the homogeneous dual-mixed tropic population is Dual_R tropic, determining that the subject would benefit from CXCR4-inhibitor therapy if the homogeneous dual-mixed tropic population is Dual_X tropic, and determining that the subject would not benefit from either CCR5-inhibitor or CXCR4-inhibitor therapy if the homogeneous dual-mixed tropic population is neither Dual_R tropic nor Dual_X tropic, wherein the population is Dual_R tropic if the population has at least 10-fold greater ability to enter cells expressing the CCR5 co-receptor relative to the population's ability to enter cells co-expressing CXCR4, and wherein the population is Dual_X tropic if the population has at least 10-fold greater ability to enter cells expressing the CXCR4 co-receptor relative to the population's ability to enter cells co-expressing CCR5, and treating the subject with an effective amount of a CCR5 inhibitor if the homogeneous dual-mixed tropic population is Dual_R tropic, treating the subject with an effective amount of a CXCR4 inhibitor if the homogeneous dual-mixed tropic population is Dual_X tropic, and treating the subject with an effective amount of an inhibitor other than a CCR5 inhibitor or a CXCR4 inhibitor if the homogeneous dual-mixed tropic population is neither Dual_R tropic nor Dual_X tropic;
   c. determining the relative proportions of CCR5-tropic, CXCR4-tropic, Dual_R tropic, Dual_X tropic, or dual tropic HIV of the heterogeneous population, wherein the HIV is Dual_R tropic if the HIV has at least 10-fold greater ability to enter cells expressing the CCR5 co-receptor relative to the HIV's ability to enter cells co-expressing CXCR4, and wherein the HIV is Dual_X tropic if the HIV has at least 10-fold greater ability to enter cells expressing the CXCR4 co-receptor relative to the HIV's ability to enter cells co-expressing CCR5; and
   d. determining whether the subject would benefit from CXCR4-inhibitor or CCR5-inhibitor therapy, comprising:
      i. determining that the subject would benefit from CCR5-inhibitor therapy if the heterogeneous population contains CCR5-tropic and/or Dual_R tropic and CXCR4-tropic and/or Dual_X tropic HIV and comprises substantially more CCR5-tropic and/or Dual_R tropic HIV than CXCR4-tropic and/or Dual_X tropic HIV, and treating the subject with an effective amount of a CCR5 inhibitor;
      ii. determining that the subject would not benefit from either CCR5-inhibitor or CXCR4 inhibitor therapy if the heterogeneous population contains CCR5-tropic and/or Dual_R tropic and CXCR4-tropic and/or Dual_X tropic HIV and comprises comparable amounts of CCR5-tropic and/or Dual_R tropic and CXCR4-tropic and/or Dual_X tropic HIV, and treating the subject with an effective amount of an inhibitor other than a CCR5 inhibitor or CXCR4 inhibitor;
      iii. determining that the subject would benefit from CXCR4-inhibitor therapy if the heterogeneous population contains CCR5-tropic and/or Dual_R tropic and CXCR4-tropic and/or Dual_X tropic HIV and comprises substantially more CXCR4-tropic and/or Dual_X tropic HIV than CCR5-tropic and/or Dual_R tropic HIV, and treating the subject with an effective amount of a CXCR4 inhibitor;
      iv. determining that the subject would benefit from CCR5-inhibitor therapy if the heterogeneous population contains CCR5-tropic and/or Dual_R tropic and dual-tropic HIV and comprises substantially more CCR5-tropic and/or Dual_R tropic HIV than dual-tropic HIV, and treating the subject with an effective amount of a CCR5 inhibitor;
      v. determining that the subject would not benefit from CCR5-inhibitor therapy if the heterogeneous population contains CCR5-tropic and/or Dual_R tropic and dual-tropic HIV and comprises relatively comparable amounts of CCR5-tropic and/or Dual_R tropic HIV and dual-tropic HIV or comprises substantially more dual-tropic HIV than CCR5-tropic and/or Dual_R tropic HIV, and treating the subject with an effective amount of an inhibitor other than a CCR5 inhibitor;
      vi. determining that the subject would benefit from CXCR4-inhibitor therapy if the heterogeneous population contains CXCR4-tropic and/or Dual_X tropic and dual-tropic HIV and comprises substantially more CXCR4-tropic and/or Dual_X tropic HIV than dual-tropic HIV, and treating the subject with an effective amount of a CXCR4 inhibitor;
      vii. determining that the subject would not benefit from either CXCR4-inhibitor or CCR-5 inhibitor therapy if the heterogeneous population contains CXCR4-tropic and/or Dual_X tropic and dual-tropic HIV and comprises relatively comparable amounts of CXCR4-tropic and/or Dual_X tropic HIV and dual-tropic HIV or comprises substantially more dual-tropic HIV than CXCR4-tropic and/or Dual_X tropic HIV, and treating the subject with an effective amount of an inhibitor other than a CCR5 inhibitor or CXCR4 inhibitor;
      viii. determining that the subject would benefit from CCR5-inhibitor therapy if the heterogeneous population contains CCR5-tropic and/or Dual_R tropic, CXCR4-tropic and/or Dual_X tropic, and dual-tropic HIV and comprises substantially more CCR5-tropic and/or Dual_R tropic HIV than CXCR4-tropic and/or Dual_X tropic and dual-tropic HIV, and treating the subject with an effective amount of a CCR5 inhibitor;
  ix. determining that the subject would not benefit from either CCR5-inhibitor or CXCR4-inhibitor therapy if the heterogeneous population contains CCR5-tropic and/or Dual_R tropic, CXCR4-tropic and/or Dual_X tropic, and dual-tropic HIV and comprises relatively comparable amounts of CCR5-tropic and/or Dual_R tropic HIV and CXCR4-tropic and/or Dual_X tropic and dual-tropic HIV, and treating the subject with an effective amount of an inhibitor other than a CCR5 inhibitor or CXCR4 inhibitor; or
  x. determining that the subject would benefit from CXCR4-inhibitor therapy if the heterogeneous population contains CCR5-tropic and/or Dual_R tropic, CXCR4-tropic and/or Dual_X tropic, and dual-tropic HIV and comprises substantially more CXCR4-tropic and/or Dual_X tropic HIV than CCR5-tropic and/or Dual_R tropic and dual-tropic HIV, and treating the subject with an effective amount of a CXCR4 inhibitor.

2. The method of claim 1, wherein the population is a homogeneous population.

3. The method of claim 2, wherein the homogeneous population is Dual_R tropic.

4. The method of claim 2, wherein the homogeneous population is Dual_X tropic.

5. The method of claim 2, wherein the homogeneous population is neither Dual_R tropic nor CXCR4-tropic.

6. The method of claim 1, wherein the population is a heterogeneous population.

7. The method of claim 6, wherein the heterogeneous population contains CCR5-tropic and/or Dual_R tropic and CXCR4-tropic and/or Dual_X tropic HIV.

8. The method of claim 7, wherein the population comprises substantially more CCR5-tropic and/or Dual_R tropic HIV than CXCR4-tropic and/or Dual_X tropic HIV.

9. The method of claim 7, wherein the population comprises comparable amounts of CCR5-tropic and/or Dual_R tropic and CXCR4-tropic and/or Dual_X tropic HIV.

10. The method of claim 7, wherein the population comprises substantially more CXCR4-tropic and/or Dual_X tropic HIV than CCR5-tropic and/or Dual_R tropic HIV.

11. The method of claim 6, wherein the heterogeneous population contains CCR5-tropic and/or Dual_R tropic and dual-tropic HIV.

12. The method of claim 11, wherein the population comprises substantially more CCR5-tropic and/or Dual_R tropic HIV than dual-tropic HIV.

13. The method of claim 11, wherein the population comprises relatively comparable amounts of CCR5-tropic and/or Dual_R tropic HIV and dual-tropic HIV.

14. The method of claim 11, wherein the population comprises substantially more dual-tropic HIV than CCR5-tropic and/or Dual_R tropic HIV.

15. The method of claim 6, wherein the heterogeneous population contains CXCR4-tropic and/or Dual_X tropic and dual-tropic HIV.

16. The method of claim 15, wherein the population comprises substantially more CXCR4-tropic and/or Dual_X tropic HIV than dual-tropic HIV.

17. The method of claim 15, wherein the population comprises relatively comparable amounts of CXCR4-tropic and/or Dual_X tropic HIV and dual-tropic HIV.

18. The method of claim 15, wherein the population comprises substantially more dual-tropic HIV than CXCR4-tropic and/or Dual_X tropic HIV.

19. The method of claim 6, wherein the heterogeneous population contains CCR5-tropic and/or Dual_R tropic, CXCR4-tropic and/or Dual_X tropic, and dual-tropic HIV.

20. The method of claim 19, wherein the population comprises substantially more CCR5-tropic and/or Dual_R tropic HIV than CXCR4-tropic and/or Dual_X tropic and dual-tropic HIV.

21. The method of claim 19, wherein the population comprises relatively comparable amounts of CCR5-tropic and/or Dual_R tropic HIV and CXCR4-tropic and/or Dual_X tropic and dual-tropic HIV.

22. The method of claim 19, wherein the population comprises substantially more CXCR4-tropic and/or Dual_X tropic HIV than CCR5-tropic and/or Dual_R tropic and dual-tropic HIV.

23. The method of claim 1, wherein the step of determining whether the HIV population is a homogeneous or heterogeneous population is performed by determining a tropism phenotype for at least about 100 HIV.

24. The method of claim 1, wherein the step of determining whether the HIV population is a homogeneous or heterogeneous population is performed by determining a tropism phenotype for at least about 112 HIV.

25. The method of claim 1, wherein the step of determining whether the HIV population is a homogeneous or heterogeneous population is performed by determining a tropism phenotype for at least about 125 HIV.

26. The method of claim 1, wherein the step of determining whether the HIV population is a homogeneous or heterogeneous population is performed by determining a tropism phenotype for at least about 137 HIV.

27. The method of claim 1, wherein the step of determining whether the HIV population is a homogeneous or heterogeneous population is performed by determining a tropism phenotype for at least about 150 HIV.

28. The method of claim 1, wherein the step of determining whether the HIV population is a homogeneous or heterogeneous population is performed by determining a tropism phenotype for at least about 162 HIV.

29. The method of claim 1, wherein the step of determining whether the HIV population is a homogeneous or heterogeneous population is performed by determining a tropism phenotype for at least about 175 HIV.

30. The method of claim 1, wherein the step of determining whether the HIV population is a homogeneous or heterogeneous population is performed by determining a tropism phenotype for at least about 187 HIV.

31. The method of claim 1, wherein the step of determining whether the HIV population is a homogeneous or heterogeneous population is performed by determining a tropism phenotype for at least about 192 HIV.

32. The method of claim 1, wherein the step of determining whether the HIV population is a homogeneous or heterogeneous population is performed by determining a tropism phenotype for at least about 200 HIV.

* * * * *